(12) United States Patent
Horwich et al.

(10) Patent No.: US 6,214,606 B1
(45) Date of Patent: Apr. 10, 2001

(54) YEAST HEAT SHOCK PROTEIN 60 AND ANALOGS

(76) Inventors: Arthur L. Horwich, 6 Tyler Ave., Branford, CT (US) 06405; Mingyuan Cheng, 35 Rogers Rd., Hamden, CT (US) 06517; Richard Hallberg, University of Basel, Department of Bio-chemistry, Klingelberg Strasse 70, CH-4056 Basel (SE); Donald S. Reading, 1115 Scott Ave.; Alan Myers, 815 Crystal St., both of Ames, IA (US) 50010

( * ) Notice: Subject to any disclaimer, the term of this patent is extended or adjusted under 35 U.S.C. 154(b) by 0 days.

(21) Appl. No.: 07/673,158

(22) Filed: Mar. 18, 1991

Related U.S. Application Data

(63) Continuation of application No. 07/261,573, filed on Oct. 24, 1988, now abandoned.

(51) Int. Cl.[7] .............................. C12N 1/15; C12N 5/10; C12N 15/11; C12N 15/63
(52) U.S. Cl. ................... 435/254.11; 435/252.3; 435/320.1; 435/325; 536/23.1; 536/23.7
(58) Field of Search ................... 435/6, 254.11, 435/252.3, 320.1, 325; 536/27, 23.1, 23.7

(56) References Cited

PUBLICATIONS

Jindal et al., *Mol. Cell. Biol.*, 9(5):2279–2283 (1989).
Mehra et al., *Proc. Natl. Acad. Sci. USA*, 83:7013–7017 (1986).
Sigma Chemical Co. catalogue Feb. 1986; pp. 844, 845 & 849.*
Ingolia et al., Molecular & Cellular Biology 2 (11) 1388–98 (1982).*
Moran et al., Can J Biochem Cell Biol 61 (6) 488–499 (1983).*
Hickey et al., Gene 43 147–154 (1986).*

\* cited by examiner

*Primary Examiner*—Robert A. Schwartzman
(74) *Attorney, Agent, or Firm*—Arnall Golden & Gregory, LLP

(57) ABSTRACT

A purified, biologically active yeast mitochondrial heat shock protein exhibiting an $M_r$ of about 60K (hsp60) and its biologically active analogs exhibiting an $M_r$ of 55K–65K are disclosed. Polynucleotide segments that encode hsp60 and its analogs are disclosed as are vectors containing the same, as well as transformed cells that contain the vectors. Methods of assembling non-functional protein subunits into a functional oligomeric protein complex and for converting an inactive form of a monomeric protein molecule or protein subunit molecule into an active form of the molecule are also disclosed.

13 Claims, 17 Drawing Sheets

```
                                                                    BclI
                                                                 ‾‾‾‾‾‾‾‾‾
                                                              5' - TGATCAAGTA
-410  GAACGCCAAGAGACTAGTTGTGTGCAAAGAAGTACAGTTGAAATTCCAGCCAGTTATGTCTC
-400  ATCCCTATTCCACTGTTTTTGTAGGTATACAATGGTGTTACGAGCATTGAAGCTGTTT
-342  ATTGCCTGGTATTACCTCTGGAAACTTACTTTATAGCCGCCCATCTGTATATGTCATC
-284  ATATACGGACCCTTGTGTGGAATTTTCCAGAAAACCAAATGGGGAGGGTGACTTTAATTTT
-226  GCTTCGTTTTGTCCGGAGCAGAATCCAGACGGACATTCATGTATATATATTGAAGGAG
-168  ACTAAGTTTTACATTATGCATTATGTAAGGTCGTGGTTGCGTCTTCATGCACTTCCTTGAA
-110  TAATATAAGAAAATTCCCACGAGAAACATCATAAGCAAAAAAGTTTTCAAA
-52
+1    ATG TTG AGA TCA TCC GTT GTT CGT AGT CGC GCT ACT TTA AGG
      Met Leu Arg Ser Ser Val Val Arg Ser Arg Ala Thr Leu Arg
```

*FIG. 1A*

+43  CCT TTA TTG CGT GCT TAC TCC TCT CAT AAA GAA TTG AAA
     Pro Leu Leu Arg Ala Tyr Ser Ser His Lys Glu Leu Lys

+85  TTC GGT GTA GAA GGA AGA GCC TCC CTT CTT AAG GGT GTC GAA
     Phe Gly Val Glu Gly Arg Ala Ser Leu Leu Lys Gly Val Glu

+127 ACT TTA GCT GAA GCG GTT GCT GCT ACT TTG GGT CCA AAG GGT
     Thr Leu Ala Glu Ala Val Ala Ala Thr Leu Gly Pro Lys Gly

+169 AGA AAC GTT TTA ATC GAA CAG CCT TTC GGT CCT CCA AAG ATT
     Arg Asn Val Leu Ile Glu Gln Pro Phe Gly Pro Pro Lys Ile

+211 ACT AAG GAT GGT GTT ACA GTT GCC AAA TCT ATT GTG TTG AAG
     Thr Lys Asp Gly Val Thr Val Ala Lys Ser Ile Val Leu Lys

+253 GAC AAG TTT GAA AAT ATG GGT GCC AAG TTA CTA CAA GAA GTT
     Asp Lys Phe Glu Asn Met Gly Ala Lys Leu Leu Gln Glu Val

+295 GCC TCC AAA ACC AAT GAG GCT GCT GGT GAC GGT ACT ACT TCT
     Ala Ser Lys Thr Asn Glu Ala Ala Gly Asp Gly Thr Thr Ser

*FIG. 1B*

```
+337  GCT ACT GTT TTA GGT AGA GCC ATC TTC ACA GAA TCC GTC AAA
      Ala Thr Val Leu Gly Arg Ala Ile Phe Thr Glu Ser Val Lys

+379  AAT GTC GCC GCT GGT TGT AAC CCT ATG GAT TTG AGA AGG GGT
      Asn Val Ala Ala Gly Cys Asn Pro Met Asp Leu Arg Arg Gly

+421  TCT CAA GTT GCA GTT GAA AAA GTG ATT GAA TTT TTG AGC GCC
      Ser Gln Val Ala Val Glu Lys Val Ile Glu Phe Leu Ser Ala

+463  AAC AAG AAA GAA ATT ACC ACA TCT GAG GAA ATT GCT CAA GTA
      Asn Lys Lys Glu Ile Thr Thr Ser Glu Glu Ile Ala Gln Val

+505  GCA ACC ATT TCT GCC AAT GGG GAC TCT CAT GTT GGT AAG TTA
      Ala Thr Ile Ser Ala Asn Gly Asp Ser His Val Gly Lys Leu

+547  CTA GCT TCA GCT ATG GAA AAG GTT GGA AAA GAA GGT GTC ATC
      Leu Ala Ser Ala Met Glu Lys Val Gly Lys Glu Gly Val Ile

+589  ACT ATC AGA GAA GGT AGA ACA TTG GAA GAT GAA CTT GAG GTT
      Thr Ile Arg Glu Gly Arg Thr Leu Glu Asp Glu Leu Glu Val
```

*FIG. 1C*

+631 ACT GAA GGT ATG AGG TTT GAT CGT GGT TTT ATT TCT CCA TAC
    Thr Glu Gly Met Arg Phe Asp Arg Gly Phe Ile Ser Pro Tyr

+673 TTC ATC ACT GAT CCA AAG TCG AGC AAG GTG GAA TTT GAA AAG
    Phe Ile Thr Asp Pro Lys Ser Ser Lys Val Glu Phe Glu Lys

+715 CCA TTG CTA TTG TTG AGT GAA AAA ATT TCT TCC ATT CAA
    Pro Leu Leu Leu Leu Ser Glu Lys Lys Ile Ser Ser Ile Gln

+757 GAT ATC TTG CCA GCT TTG GAA ATT TCC AAT CAA AGC AGA AGA
    Asp Ile Leu Pro Ala Leu Glu Ile Ser Asn Gln Ser Arg Arg
            BclI

+799 CCT TTG TTG ATC ATT GCT GAA GAT GTT GAC GGT GAA GCT CTT
    Pro Leu Leu Ile Ile Ala Glu Asp Val Asp Gly Glu Ala Leu

+841 GCG GCC TGT ATT TTG AAC AAG TTA AGG GGT CAA GTT AAG GTT
    Ala Ala Cys Ile Leu Asn Lys Leu Arg Gly Gln Val Lys Val

+883 TGT GCT GTG AAG GCG CCT GGT TTC GGT GAT AAT AGA AAG AAT
    Cys Ala Val Lys Ala Pro Gly Phe Gly Asp Asn Arg Lys Asn

*FIG. 1D*

```
+925   ACA ATT GGT GAT ATT GCA GTC TTG ACG GGC GGT ACT GTT TTT
       Thr Ile Gly Asp Ile Ala Val Leu Thr Gly Gly Thr Val Phe

+967   ACT GAG GAG TTG GAT TTG AAA CCA GAA CAA TGT ACC ATA GAA
       Thr Glu Glu Leu Asp Leu Lys Pro Glu Gln Cys Thr Ile Glu

+1009  AAC TTG GGT TCT TGT GAC TCT ATT ACC GTT ACT AAG GAA GAC
       Asn Leu Gly Ser Cys Asp Ser Ile Thr Val Thr Lys Glu Asp

+1051  ACC GTT ATC CTG AAC GGT AGT GGT CCA AAG GAA GCT ATT CAA
       Thr Val Ile Leu Asn Gly Ser Gly Pro Lys Glu Ala Ile Gln

+1093  GAG AGA ATT GAA CAA ATC AAG GGC TCC ATC AAG GAG CGT ATT CAA
       Glu Arg Ile Glu Gln Ile Lys Gly Ser Ile Lys Glu Arg Leu Ala

+1135  ACA AAT TCA TAT GAG AAG GAG AAA CTG CAA GAG CGT TTG GCC
       Thr Asn Ser Tyr Glu Lys Glu Lys Leu Gln Glu Arg Leu Ala

+1177  AAA TTG TCC GGG GGT GTT GCT GTC ATC AGG GTC GGT GGT GCA
       Lys Leu Ser Gly Gly Val Ala Val Ile Arg Val Gly Gly Ala
```

FIG. 1E

```
+1219  TCT GAA GTT GAA GTT GGT GAA AAG AAG GAC CGT TAC GAT GAT
       Ser Glu Val Glu Val Gly Glu Lys Lys Asp Arg Tyr Asp Asp
                                       PstI

+1261  GCT TTG AAC GCT ACC AGA GCT GCA GTT GAG GAA GGT ATC TTG
       Ala Leu Asn Ala Thr Arg Ala Ala Val Glu Glu Gly Ile Leu

+1303  CCA GGT GGT GGT ACT GCC TTA GTG AAG GCA TCT AGA GTT TTG
       Pro Gly Gly Gly Thr Ala Leu Val Lys Ala Ser Arg Val Leu
                                SalI

+1345  GAT GAA GTT GTT GTC GAC AAT TTC GAT CAA AAA TTG GGT GTC
       Asp Glu Val Val Val Asp Asn Phe Asp Gln Lys Leu Gly Val

+1387  GAT ATC ATA AGA AAG GCC ATT ACA AGA CCA GCC AAG CAG ATC
       Asp Ile Ile Arg Lys Ala Ile Thr Arg Pro Ala Lys Gln Ile

+1429  ATT GAA AAC GCT GGT GAA GAA GGT TCA GTT ATC ATC GGC AAA
       Ile Glu Asn Ala Gly Glu Glu Gly Ser Val Ile Ile Gly Lys

+1471  TTG ATT GAT GAA TAT GGT GAT GAT TTT GCC AAG GGT TAC GAT
       Leu Ile Asp Glu Tyr Gly Asp Asp Phe Ala Lys Gly Tyr Asp
```

*FIG. 1F*

+1513  GCC TCT AAG TCA GAA TAC ACC GAC ATG TTA GCC ACT GGT ATC
       Ala Ser Lys Ser Glu Tyr Thr Asp Met Leu Ala Thr Gly Ile

+1555  ATC GAT CCA TTT AAA GTG GTT AGA TCC GGT TTA GTT GAT GCT
       Ile Asp Pro Phe Lys Val Val Arg Ser Gly Leu Val Asp Ala

+1597  TCT GGT GTT GCC TCA CTA TTA GCT ACT ACC GAA GTT GCT ATT
       Ser Gly Val Ala Ser Leu Leu Ala Thr Thr Glu Val Ala Ile

+1639  GTT GAT GCC CCA GAA CCA CCA GCA GCT GCT GGC GCT GGT GGT
       Val Asp Ala Pro Glu Pro Pro Ala Ala Ala Gly Ala Gly Gly

+1681  ATG CCA GGT GGT ATG CCA GGA ATG CCA GGT ATG ATG TAA CGA
       Met Pro Gly Gly Met Pro Gly Met Pro Gly Met Met >>>

+1723  CCGCCTTAATTCAAAATTTATCTTTCTTTAAATATGGTAATAATTTATTATCTT

+1775  GTAAAT - 3'

FIG. 1G

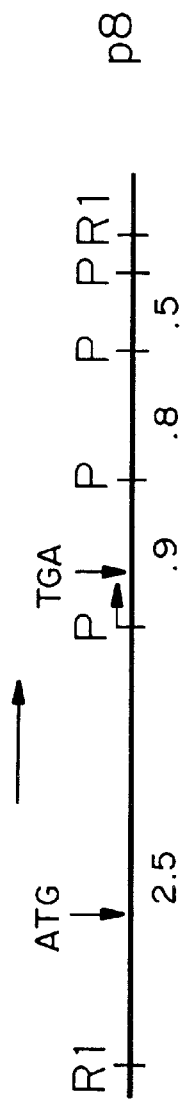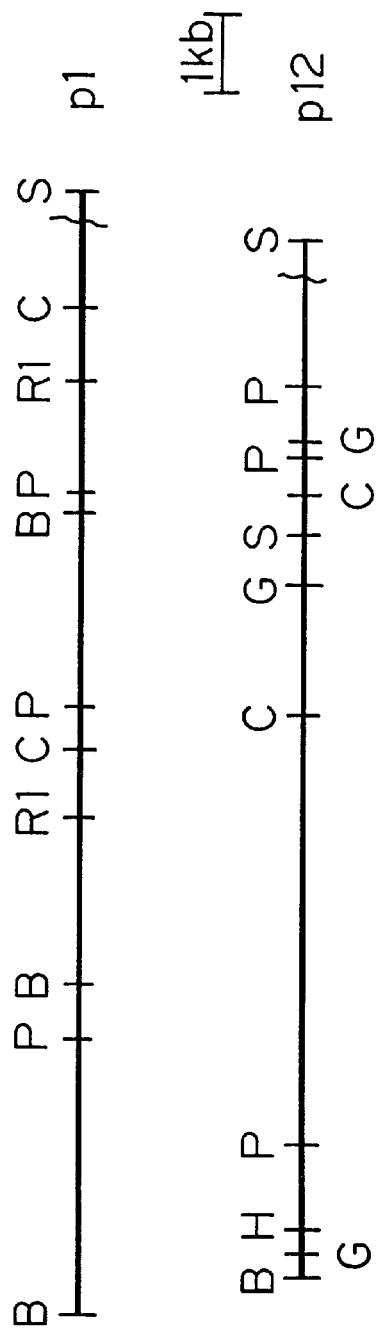
FIG. 5B    FIG. 5C    FIG. 5D

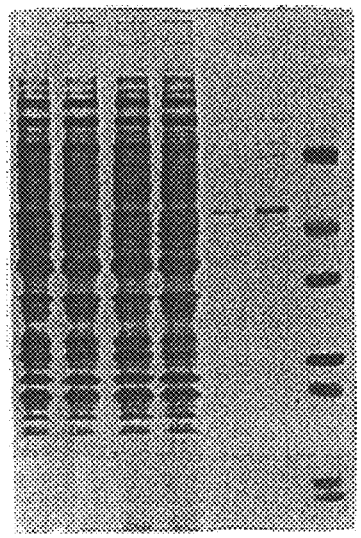
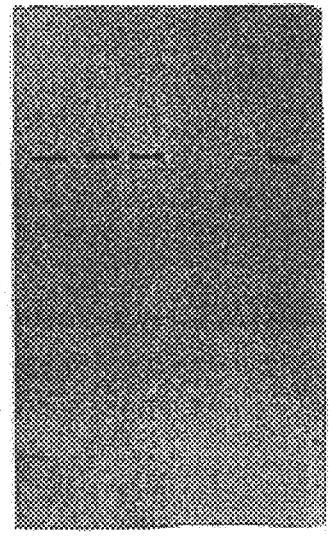
*FIG. 6A*  *FIG. 6B*
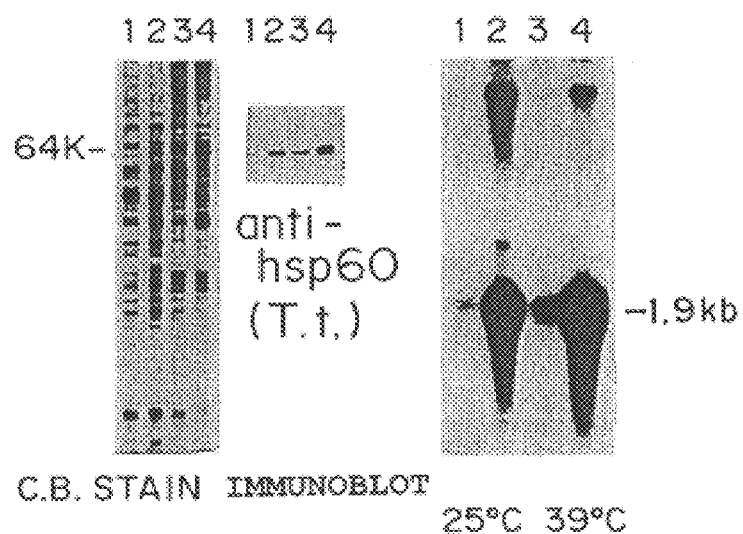
*FIG. 7A*  *FIG. 7B*

```
groEL:                              M A A K D V K
hsp60: M L R S S V V R S R A T L R P L L R R A Y S S H K E L K
RBP:                                      G A D A K E I A groEL:   F G N D A R V K M L R G V N V L A D A V K V T L G P K G
hsp60:   F G V E G R A S L L K G V E T L A E A V A A T L G P K G
RBP:     F D Q K S R A A L Q A G V E K L A N A V G V T L G P R G groEL:   R N V L D K S F G A P T I T K D G V S V A R E I E L E
hsp60:   R N V L I E Q P F G A P K I T K D G V T V A K S I V L
RBP:     R N V L D E - Y G N P K V V N D G V T I A R A I E L A groEL:   D K F E N M G A Q M V K E V A S K A N D A A G D G N N T
hsp60:   D K F E N M G A K L L Q E V A S K T N D A A G D G T T
RBP:     N P M E N A G A A L I R E V A S K T N D S A G D G T T groEL:   A T V L A Q A I I T E G L K A V A A G M N P M D L K R G
hsp60:   A T V L G R A I F T E S V K N V A A G C N P M D L R R G
RBP:     A C V L A R E I H K L G I L S V T S G A N P V S L K K G
```

FIG. 9A

```
groEL:  I D K A V T A A V E E L K A L S V P C S D S K A I A Q V
hsp60:  S Q V A V E K V I E F L S A N K K E I T T S E E I A Q V
RBP:    I D K T V Q G L I E E R K A R P V K G S G D I K A V groEL:  G T I S A T S D E T V G K L I A E A M D K V G K E G V I
hsp60:  A T I S A N G D S H V G K L L A S A M E K V G K E G V I
RBP:    A S I S A G N D E L I G A M I A D A I D K V G P D G V L groEL:  T V E D G T G L Q D E L D V V E G M Q F D R G Y L S P Y
hsp60:  T I R E G R T L E D E L E I T E G M R F D R G Y I S P Y
RBP:    S I E S S S F E T T V D E E G M E I D R G Y I S P Q groEL:  F I N K P E T G A V E L E S P F I L L A D K K I S N I R
hsp60:  F I T D P K S S K V E F E K P L L L S E K K I S S I Q
RBP:    F V T N L E K S I V E F E N A R V L I T D Q K I T S I K groEL:  E M L P V L E A V A K A G K P L L I I A E D V E G E A L
hsp60:  D I L P A L E I S N Q S R R P L L I I A E D V D G E A L
RBP:    E I H P L L E Q T T Q L R C P L F I V A E D I T G E A L
```

FIG. 9B

```
gloEL:  ATAVVNTIRGIVKVAAVKAPGFGDRRKA
hsp60:  ACILNKLRGQVKVCAVKAPGFGDNRKN
RBP:    ATLVVNKLRGINVAAIKAPSEGERRKA gloEL:  MLQDIATLTGGTVISEEIGMELEKATLE
hsp60:  TIGDIAVLTGGTVFTEELDLKPEQTIE
RBP:    VLQDIAIVTGAEYLAKDLGLLVENATVD gloEL:  DLGQAKRVVINKDTTTIDGVGEEAAIQ
hsp60:  NLGSCDSITVTKEDTVILNSGPKEAIQ
RBP:    QLGTARKITIHQTTTLIADAASKDEIQ gloEL:  GRVAQIRQQIEEAT-SDYDREKLQERVA
hsp60:  ERIEQLKGSIDITTNSYEKEKLQERLA
RBP:    ARVAQLKKELSE-TDSIYDSEKLAERIA gloEL:  KLAGGVAVIKVGAATEVEMKEKKARVED
hsp60:  KLSGGVAVIRVGGASEVEVGEKKDRYDD
RBP:    KLSGGVAIKVGATTETELEDRQLRIED
```

FIG. 9C

```
gloEL:  A L H A T R A A V E E G V V A G G G V A L I R V A S K L
hsp60:  A L N A T R A A V E E G I L P G G G T A L V K A S R V L
RBP:    A K N A T F A A I E E G I V P G G G A A Y V H L S T Y V gloEL:  A D L R G - - Q N E D Q N V G I K V A L R A M E A P L R
hsp60:  D E V V - - D N F D Q K L G V D I R K A I T R P A K
RBP:    P A I K E T I E D H D E R L G A D I I Q K A L Q A P A S gloEL:  Q I V L N C G E E P S V V A N T V K - - G G D G N Y G
hsp60:  Q I H I E N A G E E G S V I H G K L I D E Y G D D F A K G
RBP:    L I A N N A G V E G E V V I E K I K E S E W E M - - I G gloEL:  Y N A A T E E Y G N M I D M G I L D P T K V T R S A L Q
hsp60:  Y D A S K S E Y T D M L A T G H I D P F K V R S G L V
RBP:    Y N A M T D K Y E N L I E S G V I D P A K V T R C A L Q gloEL:  Y A A S V A G L M I T T E C M V T D L P K N D A A D L G
hsp60:  D A S G V A S L L A T T E V I V D A P E P P A A A - G
RBP:    N A A S V S G M V L T T Q - A I V V E K P K P K V A
```

FIG. 9D gloEL:  A  A  G G M  G G M -  G G M  G M M
hsp60:  A  -  G G M  G G M P  G G M  G M M
RBP:    E  P  A E G Q  L S V  G P M  P G M

FIG. 9E

YEAST HEAT SHOCK PROTEIN 60 AND ANALOGS

This is a continuation of U.S. Ser. No. 07/261,573 filed Oct. 24, 1988 now abandoned.

This invention was made with the support of the Government of the United States of America and the Government of the United States of America has certain rights to this invention.

DESCRIPTION

1. Technical Field

The present invention relates to yeast heat shock protein 60 (hsp60) and analogs thereof that are useful in assembling biologically active proteins.

2. Background of the Invention

The translocation of proteins through biological membranes is a phenomenon of fundamental importance, enabling the compartmentation of eurcaryotic cells. Recent studies of protein translocation have focused on determination of the tertiary structure of proteins that are translocated, and on identification of mediating components. Particular attention has been directed to mitochondria because most of the proteins residing inside these organelles are initially synthesized outside, in the cytosol, and then translocated to the innermost matrix compartment.

Several studies have indicated that newly-synthesized mitochondrial precursor proteins must assume an "unfolded" conformation in order to be translocated, and a recent analysis suggests that this translocation-competent conformation may be directed by a family of hsp70 proteins in the cytosol. After passage through the mitochondrial membranes at points of contact between outer and inner membranes, and following subsequent proteolytic removal of $NH_2$-terminal signal peptides, mitochondrial subunits fold or assemble (fold/assemble) into their biologically active conformations. This step might not occur spontaneously but rather it might be an active step, requiring the action of one or more gene products. If such products exist, the gene products may be necessary to produce functional conformations of biologically active molecules which are chemically synthesized or produced recombinantly in a host cell lacking the gene product.

Hemmingsen et al. [*Nature*, 333:330–334 (1988)] describe a family of proteins they term "molecular chaperones" which are associated with post-translational assembly of proteins. The proposed role of the chaperones is to ensure that the folding of certain polypeptides and their assembly into oligomeric structures occurs correctly, presumably by preventing formation of "improper" structures resulting from the exposure of hydrophobic or charged surfaces either within or between polypeptide chains. The authors state that the three classes recognized within the molecular chaperone family are (1) nucleoplasmin, (2) hsp70-immunoglobulin heavy chain binding protein class, and (3) the bacterial-mitochondrial-chloroplast class. The authors propose the term "chaperoning" to apply to the third class.

Hemmingsen et al. suggest that those biotechnologists encountering problems or producing foreign proteins in bacterial cells may be experiencing a failure of a bacterial chaperonin to be able to mediate folding/assembly normally performed by a chloroplast or mitochondrial chaperonin.

Determining those proteins necessary for proper folding/assembly of foreign proteins in a host cell would facilitate production of active, biologically useful proteins.

BRIEF SUMMARY OF THE INVENTION

The present invention has several facets. Those facets revolve around a yeast (*S. cerevisiae*) heat shock protein that plays a pivotal role in protein assembly and/or activation, particularly for mitochondrial proteins.

In one aspect, the invention contemplates a purified, biologically active protein having an $M_r$ of about 55,000 to about 65,000 daltons in sodium dodecyl sulfate-polyacrylamide gel electrophoresis. That protein exhibits at least about 60 percent amino acid residue identity to the yeast mitochondrial heat shock protein whose amino acid residue sequence is shown in FIG. 1 from amino acid residue position 23 through position 572. That yeast protein is referred to herein as hsp60 or an analog thereof.

The invention further contemplates a DNA segment consisting essentially of an isolated, non-chromosomal DNA segment containing sufficient DNA to encode hsp60 or an analog. The DNA segment typically contains about 1600 to about 2300 base pairs, and preferably encodes the amino acid residue sequence shown in FIG. 1 from nucleotide position 67 through nucleotide position 1716.

Another embodiment of the invention contemplates a vector capable of autonomous replication in a cell. The vector contains an operatively linked polynucleotide sequence segment that encodes hsp60 or an analog thereof. The vector is preferably a DNA vector that directs expression of hsp60 or its analog.

Still another embodiment contemplates a transformed host cell containing an above-described vector. That host cell can be eucaryotic or procaryotic.

Yet other embodiments of the invention relate to methods.

In a first method, a functional oligomeric protein complex is formed. Here, non-functional protein subunits are admixed in vitro with a functionalizingly effective amount of a biologically operative aqueous yeast mitochondrial matrix preparation to form an aqueous admixture. That matrix preparation contains at least about twice the amount of hsp60 or an analog than the amount of hsp60 present after heat shock up to about 10 percent of the total protein in the matrix preparation. The admixture is maintained under biological culture conditions for a time period sufficient for the non-functional protein subunits to bind to hsp60 or analog, be processed and folded, and to dissociate therefrom to form a functional oligomeric protein complex.

In a second method, an inactive form of monomeric protein molecules or protein subunit molecules is converted to an active form. In this method, inactive monomeric protein molecules or protein subunit molecules are admixed in vitro with an activatingly effective amount of a biologically operative, aqueous yeast mitochondrial matrix preparation as discussed before, to form an aqueous admixture. The admixture is maintained under biological culture conditions for a time period sufficient for the inactive monomeric protein molecules or inactive protein subunits to bind to hsp60 or its analog, be processed and folded, and to dissociate to form an active form of the monomeric protein molecules or protein subunit molecules.

Third and fourth methods are substantially identical to the above first and second methods, respectively, except that the mitochondrial matrix preparation is used as is and does not include added hsp60 or an analog protein molecule.

In each of the above-discussed methods, the non-functional protein subunits, or inactive monomeric protein molecules or inactive protein subunit molecules are typically present at a weight ratio relative to the total protein of the matrix preparation of about 1 to about 20 parts relative to about 200 to about 2000 parts, respectively. The total protein concentration of an aqueous admixture is about 10 to about 70 milligrams per milliliter.

BRIEF DESCRIPTION OF THE DRAWINGS

In the Figures forming a portion of this disclosure:

FIG. 1, in seven parts (FIGS. 1A, 1B, 1C, 1D, 1E, 1F, and 1G), shows the single strand, coding nucleic acid and translated amino acid residue sequences of hsp60. Both sequences are shown from left to right and in the direction from 5'- to 3'-position and amino-terminus to carboxy-terminus, respectively. Position −410 is the BclI restriction endonuclease cleavage point at the 5'-terminus, with additional PstI, SalI and BclI restriction sites noted within the DNA sequence. Position +1 indicates the initial Met residue of the leader peptide that is fused to the protein sequence. The primary source of DNA for sequence analysis was the 5.3 kb (approximately 5 kb) EcoRI-EcoRI fragment shown in FIGS. 9A, 9B, 9C, 9D, and 9E. Segments of this fragment were subcloned into vectors pUC118 or pUC119 [Vieira et al., Meth. Enzy., 153:3–11 (1987)] and sequenced by the chain termination method. Subfragments for sequence analysis were generated by exonucleolytic digestion with Ba131 and recloned into pUC vectors. The sequences of both DNA strands were determined, and all restriction sites used for subcloning were crossed.

GalOTC/RP11 was mutagenized with ethyl methane sulfonate (EMS) and mutants were selected that were temperature-sensitive for growth on both YPEG (1 percent yeast extract, 2 percent bactopeptone, 2 percent ethanol and 3 percent glycerol) and YPD (1 percent yeast extract, 2 percent bactopeptone and 2 percent glucose). Individual mutants cultured in 1 ml YPEG at 23° C. were shifted to non-permissive temperature (37° C.) and simultaneously transferred into medium containing 2 percent galactose to induce expression of OTC.

After 2 hours, spheroplasts were prepared using 1,2 M sorbitol, 20 mM potassium phosphate (Kpi) pH 7.4, 0.17 percent mercaptoethanol and 0.05 mg/ml Zymolyase 100T (Miles). Spheroplasts were then harvested by centrifugation at 2000 r.p.m. for 5 minutes in a clinical centrifuge, and resuspended in 100 ul lysis buffer (20 mM Hepes pH 7.4 and 0.1 percent Triton-100). 50 Microliter (ul) cell lysates were assayed for OTC activity, and temperature sensitive (ts) mutants exhibiting no OTC activity were further analyzed by immunoblotting. 50 Microliter cell lysates were extracted with Laemmli buffer, electrophoresed in an 8 percent SDS-polyacrylamide gel, transferred to nitrocellulose paper and immunoblot analysis carried out with anti-OTC or anti-F1-beta-ATPase antibody [Cheng et al., Proc. Natl. Acad. Sci. USA, 84:4063–4067 (1987)].

ts Mutants predominantly producing mature OTC subunit but no OTC activity were candidates for PALO [delta-N-(phospho-acetyl)-L-ornithine] column analysis. Five optical density (O.D.) units of cells were shifted to non-permissive temperature, induced with galactose, and spheroplated as described above. Spheroplasts were lysed in 20 mM Hepes pH 7.4, 30 ug/ml Lubrol, and then applied to PALO columns. The columns were then washed with 40 mM KCl and eluted with 10 mM carbamyl phosphate. Each eluted fraction was immunoprecipitated with anti-OTC antiserum, electrophoresed, immunoblotted with anti-OTC antiserum, and visualized with radiolabeled S. aureus protein A.

Mutants in which mature OTC subunit failed to bind PALO column were selected for genetic analysis. They were backcrossed with the parental wild-type strain RP11 to segregate the ts phenotype from the inserted human OTC. Strains bearing a single ts mutation were transformed with a new GalOTC plasmid and the backcrossed with wild-type GalOTC/RP11 to study the consegregation of the ts phenotype and ts assembly defect (PALO column).

Figure 2:
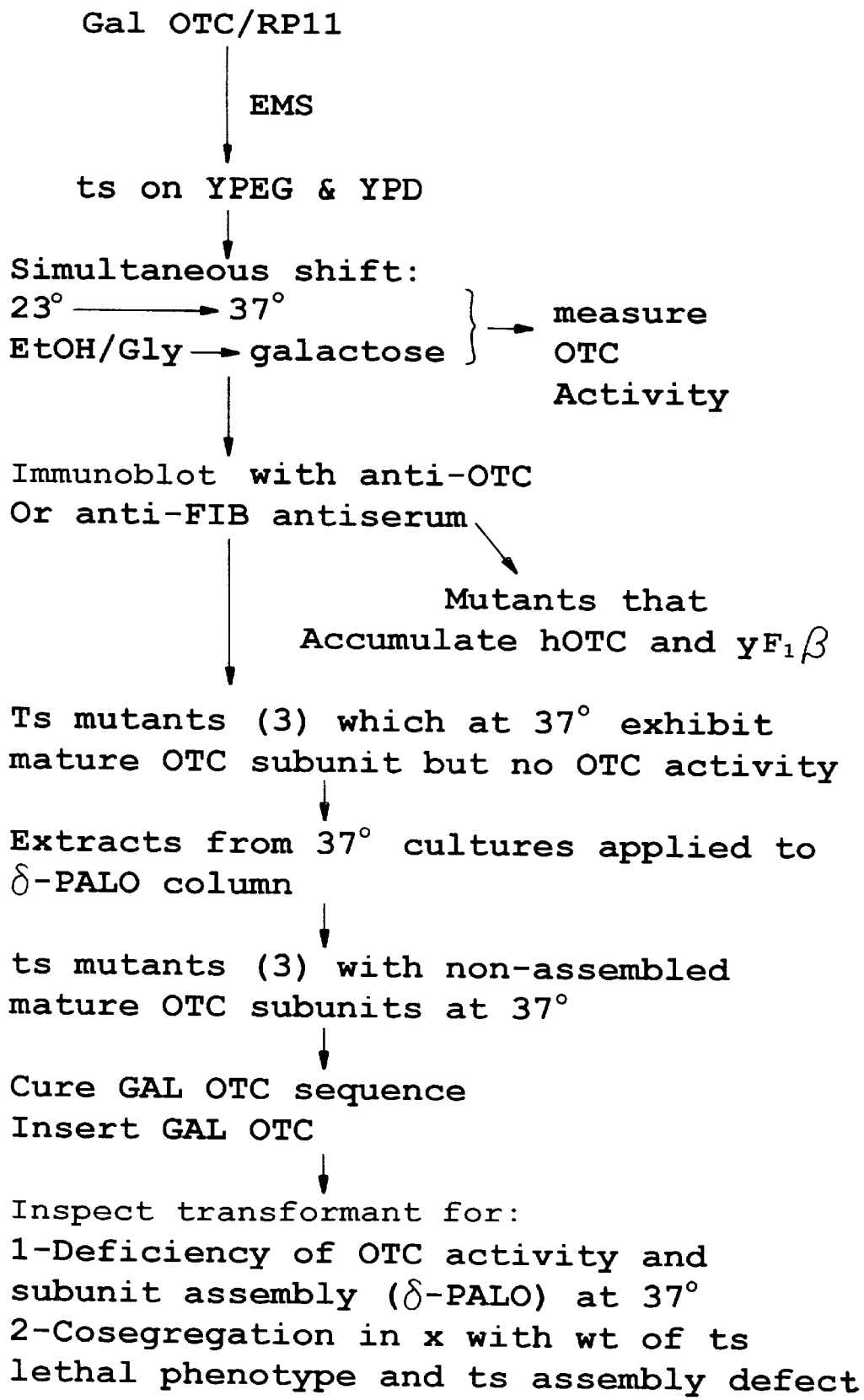
FIG. 2 illustrates a schematic representation of the scheme for isolation of S. cerevisae yeast mutants defective in assembly of mitochondrial proteins. A yeast strain, RP11, [Cheng et al., Proc. Natl. Acad. Sci., USA, 84:4063–4067 (1987)], deficient of the endogenous cytosolic ornithine transcarbamylase (OTC) was transformed with a plasmid containing the coding sequence for human OTC joined with a GalI promoter (GalOTC) [Cheng et al., Proc. Natl. Acad. Sci. USA, 84:4063–4067 (1987)]. When induced with 8 percent galactose, this transformed strain (GalOTC/RP11) has been shown to exhibit OTC enzymatic activity in the mitochondrial matrix where human OTC normally localizes [Cheng et. al., Proc. Natl. Acad. Sci., USA, 84:4063–4067 (1987)].
Figure 3A:
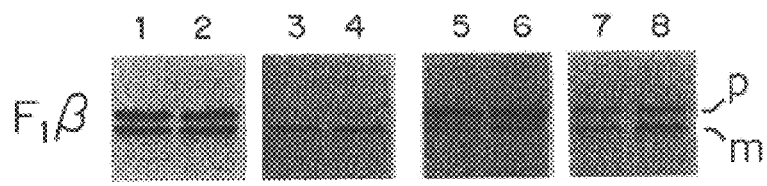
Figure 3B:
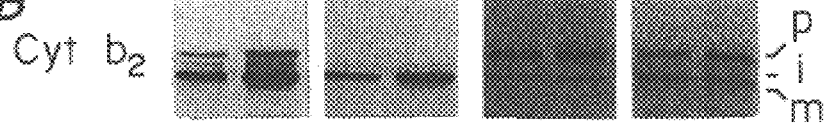

FIG. 3A and 3B contain panels, A, B, and C that illustrate studies with the alpha-143 (or ts143) mutant obtained using the scheme of FIG. 2.

Panel A is a photograph of an SDS-PAGE autoradiographic analysis for water and chloroform ($CHCl_3$) extractions of F1-beta-ATPase in wild-type (wt) and ts143 cellular extracts. Here, wild-type (wt), GalOTC/RP11, and the mutant ts143 were grown in minimal galactose medium with the required amino acids (0.67 percent yeast nitrogen base without amino acid, 2 percent galactose, 20 ug/ml histidine, 20 ug/ml leucine and 20 ul/ml arginine) to O.D.$_{600}$=0.5. Four O.D. units of cells were resuspended in 2 ml minimal galatose medium and shifted to 37° C. for 2 hours. 400 uCi $^{35}S$ methionine were then added to each culture and the culture incubated for 30 minutes. The reaction was stopped by adding $NaN_3$ to 10 mM. Twenty-five O.D. units of nonlabelled cells were then added as carrier for crude cellular fractionation.

Cells were spheroplasted in 5 ml Zymolyase solution as in FIG. 2 for 30 minutes, harvested, washed once with ice-cold 1.4 M sorbitol and 20 mM potassium phosphate (Kpi) pH 7.4, and 10 mM $NaN_3$ and then resuspended in 5 ml ice-cold 0.6 M sorbitol, 20 mM Hepes pH 7.4, 4.10 mM $NaN_3$, and 1 mN PMSF (phenylmethylsulfonyl fluoride). Spheroplasts suspensions were Dounce homogenized and centrifuged in an SS-34 rotor at 1000×g for 5 minutes at 4° C. to remove nuclei and cell debris. Supernatants were collected and centrifuged in SS-34 rotor 10,000×g for 10 minutes at 4° C. Pellets were collected and resuspended in 0.6 M sorbitol buffer as a crude mitochondrial fraction. $5 \times 10^6$ total c.p.m. of wild-type and $10 \times 10^6$ total c.p.m. of ts143 mitochondrial fractions were adjusted to 100 ul with 0.6 M sorbitol buffer and extracted with 50 ul chloroform by vertexing 1 minute.

About 7.5 percent of total counts in wild-type and 4.5 percent in ts143 were in the aqueous phase where intact F1-beta-ATPase is extracted. $0.3 \times 10^6$ c.p.m. of aqueous phase of chloroform extracts from both wild-type and ts143 were boiled in 50 ul of 4 percent SDS for 5 minutes, 1 ml of TNTE (20 mM Tris pH 7.8, 150 mM NaCl, 1 percent Triton-100, and 5 mM EDTA) was added. Immunoprecipitation was carried out with anti-F1-beta-ATPase antiserum, and the precipitates were analysed by SDS-PAGE and autoradiography. Lane (−)=immunoprecipitation of $1 \times 10^6$ c.p.m. of crude mitochondrial fractions. Lane ($CHCl_3$)= immunoprecipitation of $0.3 \times 10^6$ c.p.m. of aqueous phase of chloroform extracts. Markers on the left side of the panel indicate molecular weights of the presurser (p) and mature (m) forms.

Panel B is another photograph of an SDS-PAGE autoradiographic analysis, this time for cytochrome b2 in wild-type (wt) and ts143 cellular extracts. Wild-type (wt) and ts143 cells were cultured in minimal galactose medium with the required amino acids as described above. Two O.D. units of cells were used for in vivo $^{35}$S-methionine labeling (200 mCi/2 O.D. units of cells), as above. Cells were spheroplasted, harvested and extracted in 50 ul of 4 percent SDS. Extracts were resuspended in 1 ml TNTE and immunoprecipitated with anti-cytochrome b2 antiserum. SDS-PAGE analysis and autoradiography were as indicated before. Markers on the left side of the panel indicate molecular weights of the precursor (pre), intermediate (i) and mature (m) forms of the enzyme.

FIGS. 4A–4B is a photograph of PAGE analyses obtained from sucrose gradient sedimentations of cell extracts of ts143 cells growing at 25° C. or those cells subjected to a 25 minute, 37° C., heat shock. A culture of ts143 cells at 25° C. was split in half. One-half remained at 25° C. while the other was transferred to a 37° C. water bath. The temperature within the culture was monitored periodically, taking about 5 minutes to reach 37° C. Once reaching 37° C., the transferred cells were kept at 37° C. for an additional 25 minutes. Cells from both flasks were collected, washed, opened, and treated with Triton-DOC to lyse any remaining mitochondria. These extracts were spun at 1000×g, and the resulting supernate was then spun at 15,000×g for 15 minutes.

The 15,000×g pellet was dissolved in Laemmli buffer and supernate was overlain on a 15–30 percent sucrose gradient which was spun at 27,500 r.p.m. for 17 hours. Proteins in fractions from the sucrose gradient were precipitated and the contents subsequently dissolved in Laemmli buffer. Proteins from each fraction were separated on a 12.5 percent acrylamide gel. Two gels were run: one for stain which contained the gradient fractions and molecular weight markers (MW); the other for immunoblotting contained the gradient fractions and a sample of the 15,000×g pellet (indicated by P) containing the same cellular equivalents as each fraction represented. The proteins in the second gel were transferred to nitrocellulose for a western analysis using the anti-Tetrahymena-hsp58 antiserum. [McMullin et al., *Mol. Cell. Biol.*, 7:4414–4423 (1987)]. This anti-serum is also referred to herein as anti-hsp60 (T.t.). The arrow indicates the position of the stained yeast hsp60 complex. The direction of sedimentation is from left to right.

Figure 5A:

FIGS. 5A–5D illustrate an agarose gel separation of RNA, as well as three schematic representations of restriction maps FIG. 5B, FIG. 5C and FIG. 5D for three plasmids (p8, p1 and p12) that are capable of rescuing the ts143 mutant after transformation of that mutant with each of the plasmids. Each plasmid is from a CEN library [Rose et al., *Gene*, 60:237–243 (1987)] that contained fragments of yeast genomic DNA inserted into plasmid YCp50. Only the inserted yeast DNA of each plasmid is shown, except for a small portion of vector from the vertical wavy line to the SalI site. In each representation: B=BamHI; G=BglII; C=ClaI; R1=EcoRI; H=HindIII; P=PstI; and S=Sal I.

More specifically as to part A, wild-type yeast cells were grown in YPEG medium at 23° C. to mid-log phase. 4×10$^8$ Cells were then resuspended in 70 ml of that medium. One-half of that cell culture was grown at 23° C. and the other one-half grown at 42° C., each for 30 minutes. 5×10$^9$ Cells from each culture were harvested and used for preparation of polyA+ RNA. Total yeast RNA was prepared according to the method of Davis et al., *A Manual For Genetic Engineering Advanced Bacterial Genetics*, Cold Spring Harbor Laboratory, Cold Spring Harbor, N.Y. (1980). PolyA+ RNA was isolated using oligod(T) cellulose [Maniatis et al., *Molecular Cloning, A Laboratory Manual*, Cold Spring Harbor Laboratory, Cold spring Harbor, N.Y. (1982)]. The resulting RNA was fractionated on a 1 percent agarose gel, and transferred to nitrocellulose and hybridized with a nick-translated 0.9 kb PstI fragment derived from plasmid p8 (discussed below) following the procedures of Lerach et al., *Biochemistry*, 16:4743–4751 (1977).

The restriction map of the plasmid p8 insert is identical to that of the lambda-gt11 phage insert discussed in FIGS. 8A, 8B, and 8C hereinafter. An approximately 5 kb EcoRI-EcoRI fragment (FIGS. 1A, 1B, 1C, 1D, 1E, 1F, and 1G) derived from plasmid p8 was further analyzed by digestion with endonuclease PstI, and the fragment sizes compared to those obtained from that lambda-phage. The fragment order was found to be that indicated from the sequence of the lambda-phage.

A 900 bp PstI fragment of the insert to plasmid p8 was sequenced as indicated by the arrow. That sequence matched the sequence from the lambda-phage insert. The translational start (ATG) and stop codons (TGA) and direction of translation as determined from that lambda-phage insert as shown.

Figure 4:
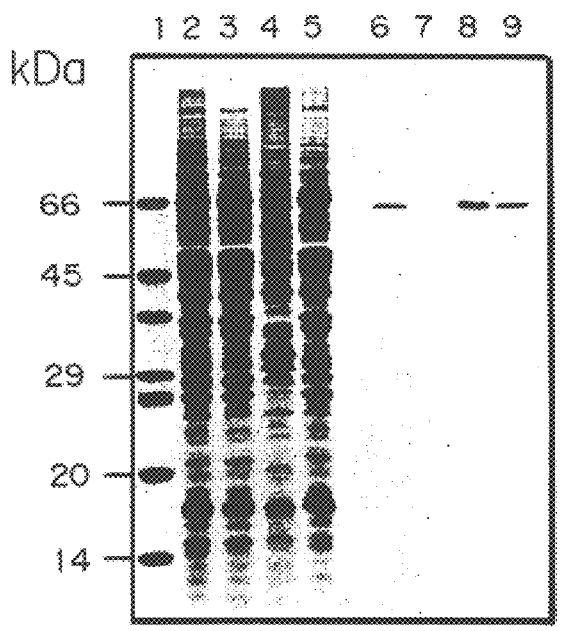

FIG. 6A and FIG. 6B are photographs of PAGE analyses similar to those of FIG. 4. The treatment of the cells was the same as above in FIG. 4 except that the cells transferred to 37° C. were kept there for 2 hours. Cell extracts were made as above but the analysis was as follows. After the initial cell breakage, a small sample was taken and an equal volume of 2 X Laemmli sample buffer was added to it. The remaining material was centrifuged as above. A small sample of the 15,000×g supernate was taken and an equal volume of 2 X Laemmli buffer was added to it. The pellet was redissolved in the same volume of initial homogenization buffer as the recovered 15,000×g supernate and a sample of this was removed and added to an equal volume of 2 X Laemmli sample buffer. Equal volumes (containing equal cell equivalents) of each of the total (TOT) extracts, 15,000×g supernates (SUP) or 15,000×g pellets (PEL) from cells at 25° C. or those at 37° C. for 2 hours, were separated on 12.5 percent acrylamide gels. FIG. 6A contains the stained gel. FIG. 6B is a western blot analysis of an identically run gel probed with the anti-hsp58 antiserum. Note that the additional protein accumulated during the 37° C. heat shock is processed perfectly normally. These results indicate that the old hsp64 complex breaks down and the new material does not assemble correctly, even though it must be imported and processed correctly. The numerals "25" and "37" at the tops of lanes indicate cells grown at 25° C. or 37° C., respectively.

FIGS. 7A and 7B illustrate SDS-PAGE analyses of cells containing single or multiple copies of HSP60. In FIG. 7A, haploid strain aW303 (kindly provided by R. Rothstein, College of Physicians and Surgeons, Columbia University, New York, N.Y.; lanes 1, 3) or the same strain transformed with plasmid vector YEpHsp60 (discussed in FIGS. 8A, 8B, and 8C) (lanes 2, 4) were grown to mid-log phase at 30° C. Sixty micrograms (ug) of total protein extracts [Hurd et. al., *Mol. Cell. Biol.*, 7:3673–3677 (1987)] (lanes 1, 2) or purified mitochondria [Faye, et al., *J. Mol. Biol*, 88:185–203 (1974)] (lanes 3, 4) were run in duplicate SDS-PAGE gels. Proteins in one gel were stained with Commassie blue (C.B. Stain), whereas those in the second gel were transferred to nitrocellulose paper and probed with anti-hsp60 (T.t.), as previously described (McMullin et al., *Mol. Cell. Biol.*, 7:4414–4423 (1987)). Raising the copy number of HSP60 by including the gene on a multi-copy plasmid increases the cellular level of anti-HSP60(T.t.)-reactive protein. Molecular weight standards included on the stained gel (not shown) showed the immunoreactive material to be of $M_r$60K.

FIG. 7B is a photograph of an autoradiograph that illustrates steady state levels of HSP60 mRNA in normal and heat stressed conditions. Strain aW303 (lanes 1, 3) or the same strain transformed with YEpHsp60 (lanes 2, 4) were grown to mid-log phase at 25° C. The cultures were then divided and grown for two additional hours, either at 25° C. (lanes 1, 2) or 39° C. (lanes 3, 4). Total nucleic acids were extracted [Lindquist, Nature, 293: 311–314 (1981)], denatured with glyoxal [McMaster et. al., Proc. Natl. Acad. Sci. USA, 74: 4835–4838 (1977)] and separated by agarose gel electrophoresis. Nucleic acids were transferred to nitrocellulose filters and analyzed by northern blotting, using the 3.0 kb fragment shown in FIG. 8B as a radiolabelled probe. The probe hybridizes to a single RNA band of 1.9 kb (RNA molecular weight standards not shown). The concentration of this mRNA is two to three times higher in the heat shocked cells than in the non-stressed control. Raising the copy number of HSP60 increases the steady-state level of the 1.9 kb mRNA at 25° C. and heat shock induction is again observed. The high $M_r$ band seen in lanes 2 and 4 is due to hydridization of the probe to DNA.

Figures 8A, 8B, 8C:
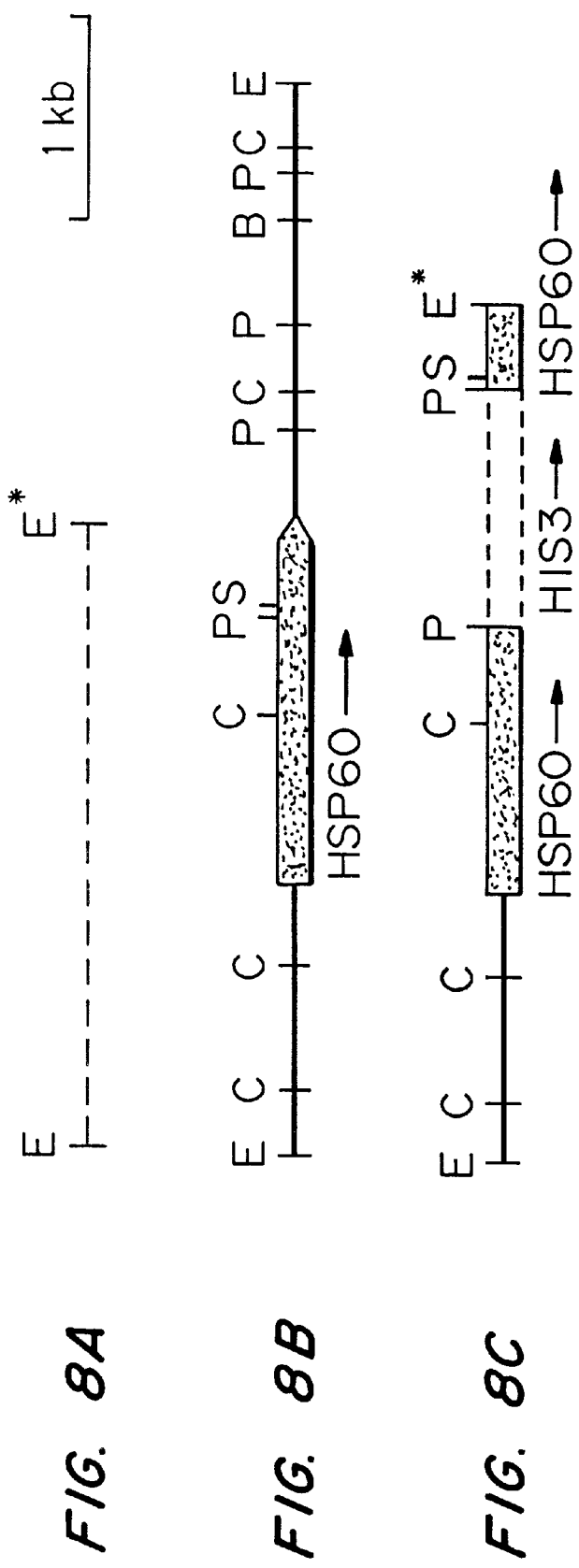

FIGS. 8A, 8B, and 8C are a three-part, (A, B, and C) schematic restriction map of HSP60 and HSP60::HlS3. In FIG. 8A, the dashed line indicates the region of yeast genomic DNA isolated from an anti-hsp60 (T.t.)-reactive lambda-gt11 clone. The EcoRI site designated E was inserted as a linker during construction of the library. FIG. 8B shows the restriction map of the genomic DNA fragment containing the fragment depicted in FIG. 8A. The black bar indicates the coding region of HSP60 as determined by nucleotide sequence analysis, with the direction of transcription indicated by the arrow. Plasmid YEpHsp60 is comprised of this 5.3 kb EcoRI-EcoRI fragment cloned in the 2 micron circle-based shuttle vector YEp352 [Hill et al., Yeast, 2:163–167 (1986)]. FIG. 8C illustrates the restriction map of the null allele HSP60::HIS3. Black bars indicate the coding regions of HSP60, and dotted lines indicate a HIS3 containing fragment that interrupts HSP60 by insertion of the PstI site. The positions of restriction enzyme recognition sites are indicated for EcoRI (E), BaII (C), PstI (P), SalI (S), and BamHI (B).

The isolated DNA and plasmids were constructed as follows. A library of yeast genomic DNA fragments in lambda-gt11 [Young et. al., Proc. Natl. Acad. Sci. USA, 80:1194–1198 (1988)] was screened with anti-hsp60(T.t.) [McMullin et. al., Mol. Cell. Boil., 7:4414–4423 (1987)]. From approximately 300,000 library recombinants screened, a single positive plaque was isolated, which upon repurification yielded only positive clones. The positive recombinant contained three EcoRI fragments within the lambda arms, one of which hydridized to a heat shock inducible mRNA. This 3.0 kb fragment is depicted in the line of FIG. 8A of the Figure.

Nucleotide sequence analysis of the ends of the 3.0 kb fragment revealed an open reading frame homologous to groEL [Hendrix, J. Mol. Biol., 129:375–392 (1979)] that continued through the site marked E* in the 5'-3' direction. Therefore, the 3.0 kb fragment was used as a hybridization probe to isolate an overlapping genomic fragment containing the entire HSP60 gene. Southern hydridization analysis showed that the 3.0 kb fragment isolated from lambda-gt11 was derived from an approximately 5.0 kb genomic EcoRI fragment. A library of approximately 5.0 kb size fractioned EcoRI fragments was prepared in the "phagemid" vector pUC118 [Viera et al., Meth Enz., 153:3–11 (1987)] and screened with the 3.0 kb fragment. Positive clones contained the 5.3 kb EcoRI-EcoRI fragment shown in the line of FIG. 8B of the Figure. Nucleotide sequence analysis (FIGS. 1A, 1B, 1C, 1D, 1E, 1F, and 1G) revealed the location of HSP60.

To construct HSP60::HIS3 the 3.0 kb EcoRI fragment shown in line of FIG. 8A was cloned into the plasmid vector YEp352E, a derivative of shuttle vector YEp352 [Hill et al., Yeast, 3:163–167 (1986)] from which the PvuII fragment containing the partial lac operon and multiple cloning site was removed and replaced with an EcoRI linker. The recombinant plasmid was linearized at the unique PstI site within HSP60 and ligated to a 1.15 kb fragment of yeast DNA containing the wild-type HIS3 gene. One of the PstI sites delimiting this fragment is located downstream of the HIS3 coding region, whereas the other PstI site is derived from the pUC18 multiple cloning site. This linear EcoRI fragment shown in the line of FIG. 8C was excised from YEp352E and used to transform the HIS3⁻–HIS3⁻ diploid a/alpha-W303 to histidine independence [Hinnen et. al., Proc. Natl. Acad. Sci. USA, 75:1929–1933 (1978)]. Southern hybridization analysis of chromosomal DNA verified that the His⁺ transformants had integrated the disrupted allele at the homologous site in one chromosome, and were of the genetic constitution HSP60/HSP60::HIS3.

FIGS. 9A, 9B, 9C, 9D, and 9E illustrate the primary amino acid residue sequence alignment of yeast mitochondrial hsp60 (hsp60) with the E.coli groEL (groEL) protein and wheat chloroplast Rubisco binding protein (RBP). The predicted amino acid residue sequence of the HSP60 gene product was aligned with the predicted sequences of the groEL and RBP proteins [Hemmingson et al., Nature, 333:330–334 (1988)] using the MFALGO program [Woodbury et. al., J. Med. Evol., 15:129–148 (1980)]. Residues shared between hsp60 and either groEL or RBP are boxed.

DETAILED DESCRIPTION OF THE INVENTION

A. Definitions

Amino Acid: All amino acid residues identified herein are in the natural L-configuration. In keeping with standard polypeptide nomenclature, J. Biol. Chem., 243:3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |

-continued

TABLE OF CORRESPONDENCE

| SYMBOL | | |
|---|---|---|
| 1-Letter | 3-Letter | AMINO ACID |
| W | Trp | L-tryptophan |
| R | Arg | L-arginine |
| D | Asp | L-aspartic acid |
| N | Asn | L-asparagine |
| C | Cys | L-cysteine |

It should be noted that all protein or amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a radical such as H and OH (hydrogen and hydroxyl) at the amino- and carboxy-termini, respectively, or a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3'- or 5'-position of the pentose it is referred to as a nucleotide. Nucleotide sequences are also read from left to right and from 5'-position to 3'-position.

Base Pair (bp): A partnership of adenine (A) with thymine (T), or of cytosine (C) with guanine (G) in a double stranded DNA molecule.

B. The Hsp60 Protein

The present invention contemplates, in one embodiment, a purified, biologically active yeast mitochondrial heat shock protein having a relative molecular mass ($M_r$) as measured by sodium dodecyl sulfate-polyacrylamide gel electrophoresis (SDS-PAGE) of about 60,000 daltons (60K) designated hsp60. Biologically active analogs are also contemplated. This protein and its analogs are substantially free from other yeast mitochondrial proteins, and are thus referred to as "purified". The amino acid residue sequence of yeast mitochondrial hsp60 is shown in FIGS. 1A, 1B, 1C, 1D, 1E, 1F, and 1G.

An analog of hsp60 has a $M_r$ of about 55 to about 65K in SDS-PAGE, and at least about 60 percent, preferably at least about 80 percent, and most preferably at least about 90 percent, of its amino acid residue sequence is identical to the sequence shown in FIGS. 1A, 1B, 1C, 1D, 1E, 1F, and 1G. In view of the differences in $M_r$ between hsp60 and an analog, insertions and deletions in the sequence are contemplated, as are the inclusion of non-conservatively substituted amino acid residues. Thus, where an analog is of a lower $M_r$ than about 60K, at least about 60 percent of the amino acid residues present are identical to those shown in FIGS. 1A, 1B, 1C, 1D, 1E, 1F, and 1G. Similarly, where the analog has an $M_r$ greater than about 60K, an alignment of the amino acid residue sequence of the analog with the sequence of FIGS. 1A, 1B, 1C, 1D, 1E, 1F, and 1G as is shown in FIG. 9 provides at least an 60 percent identity between the sequences.

A purified, biologically active hsp60 protein molecule or an analog thereof, a protein of this invention, can therefore be said to have a $M_r$ of about 55K to about 65K, measured as discussed above. That protein can also be said to exhibit at least about 60 percent amino acid identity to the yeast mitochondrial heat shock protein whose amino acid residue sequence is shown in FIGS. 1A, 1B, 1C, 1D, 1E, 1F, and 1G from amino acid residue position 23 to amino acid residue position 572.

An hsp60 analog is also immunologically cross-reactive with yeast mitochondrial hsp60; i.e., polyclonal antibodies raised to one immunoreact with the other. Monoclonal antibodies can share this cross-reactive property, but need not depending upon the epitope to which they bind.

Biologic activity of hsp60 or an analog is manifest in the ability of the protein to form a macromolecular complex that sediments at about 20–25 S in a sucrose gradient. The macromolecular complex typically exhibits an approximately circular shape having a seven-fold axis of symmetry when examined by electron microscopy. The complex also exhibits a diameter of about 10 to about 15 nanometers when so examined.

It is noted that FIG. 1 is shown in terms of nucleotide positions beginning with the A of the ATG coding for the amino-terminal Met residue as +1 (or nucleotide position 1) and an untranslated 5'-region extending to nucleotide position –410. Amino acid residue positions can be readily obtained from FIGS. 1A, 1B, 1C, 1D, 1E, 1F, and 1G by dividing the nucleotide position of the 3'-most base of a codon by three, as is well known.

The hsp60 or analog thereof can include the leader sequence or the leader sequence can be absent. The leader sequence begins at residue 1 of FIGS. 1A, 1B, 1C, 1D, 1E, 1F, and 1G and continues through residue 22 (Ser).

The entire leader sequence is not needed, and is most preferably absent so that the protein begins at amino acid residue position 23. Nevertheless, the protein can begin with residues between 1 and 22, and continue through the end of the sequence in FIGS. 1A, 1B, 1C, 1D, 1E, 1F, and 1G (residue 572). In preferred embodiments, a protein of this invention has an amino acid sequence identical to that of FIGS. 1A, 1B, 1C, 1D, 1E, 1F, and 1G from either position 1 through position 572, or from position 23 through position 572. Thus, when present, the sequence from amino acid residue position 1 through position 22 is peptide-bonded to the amino acid residue at position 23, and thereby to the remainder of the sequence through position 572.

A hsp60 protein or analogs of this invention can be isolated from yeast cells using anti-hsp60 antibody or an antibody that cross-reacts with hsp60, such as the anti-hsp (T.t) antibodies reported in McMullin et al., *Mol. Cell. Bio.*, 7:4414–4423 (1987). A method of detecting hsp60 in transformed cells is described in detail in the examples and figure descriptions. A similar method can be used to purify hsp60 or an analog using immunoaffinity chromatography, as is well known.

The isolation of a DNA sequence is also described in the examples and figure descriptions. Such sequences can be used to transform host cells to express hsp60. The expression product may be glycosylated or non-glycosylated depending on the host cell used.

The study of the conditional lethal yeast mutant ts143 described herein demonstrated that proteins entering the mitochondrial matrix space from the cytosol require a matrix protein, hsp60, in order to assume their biologically active conformations. Consistent with this essential function, hsp60 is constitutively expressed. Its classification as a heat stress protein reflects the two-to-three-fold induction increase observed in response to 42° C. incubation. This response may represent a cellular mechanism for maintaining functional conformation of mitochondrial proteins during and following heat stress.

The mechanism by which hsp60 acts to determine biologically active conformation of proteins entering the matrix space is undefined, but the presence of the protein in a macromolecular complex whose sedimentation properties are affected by mutation, suggests that a "machine" which includes other proteins is involved. Considering the double doughnut structure in which hsp60 apparently resides and the similar 14-subunit scaffold structure in GroEL residues, hsp60 may play mainly a structural role, acting as a "workbench" on which folding is carried out by other proteins with catalytic activity. Putative catalytic components might reside either within the complex or within the soluble matrix. Included among such components are the translation products of plasmids p1 and p12 discussed herein.

The mitochondrial hsp60 protein is required for cell function at normal temperature and also appears to be involved in protection against heat stress. The hsp60 protein is required for assembly within mitochondria of multiple protein subunits, some synthesized within the organelle and some in the cytoplasm, into functional oligomeric enzymes. hsp60 is the second member of the heat shock regulon that is required for biogenesis of mitochondrial enzymes. hsp70 proteins recently were shown to provide an "unfolding" function necessary for translocation into both mitochondria and the lumen of the endoplasmic reticulum [Deshaies et al.; *Nature*, 332:800–805 (1988) and Chirico et al., *Nature*, 332:805–810 (1988)]. Thus, proteins with the ability to influence higher order structure of various mitochondrial proteins are located on both sides of the organelle membrane.

C. Nucleotide Segment

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence; i.e., protein or polypeptide, for which it codes.

An important and well known feature of the genetic code is its redundancy. That is, for most of the amino acid residues used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence upon translation in an organism. Occasionally, a methylated variant of a purine or pyrimidine may be incorporated into a given nucleotide sequence. However, such methylations do not affect the coding relationship in any way.

A non-chromosomal, isolated nucleotide segment of the present invention is characterized as including a DNA sequence that encodes heat stress protein 60 (hsp60) or an analog thereof, as described previously. That is, a DNA segment of the present invention is characterized by the presence of an hsp60 or analog structural gene; i.e., a gene capable of encoding an hsp60 protein and expressing that protein in an appropriate expression system as is discussed hereinafter. The gene that encodes the hsp60 protein is termed HSP60. Preferably the gene is present as an uninterrupted linear series of codons where each codon codes for an amino acid residue found in the protein; i.e., a gene free of introns.

The naturally occurring gene for hsp60 is genomic, located on a yeast chromosome. A DNA segment of the present invention is shorter than chromosomal DNA, and is non-chromosomal.

The DNA segment of the invention is also an isolated DNA molecule that is free from the yeast chromosome and substantially all of the DNA of a yeast chromosome. Isolation of a DNA segment of the invention is discussed herein. Such isolated DNA segments are typically found in an artifically-made vector as is used in recombinant DNA technology.

More particularly, the present invention contemplates a DNA segment containing a sufficient number of base pairs (bp) to encode hsp60 or an analog thereof.

Such a sufficient number is about 1650 bp for the mature protein and about 1716 for the protein plus leader sequence. In preferred practice, the DNA segment contains about 1750 to about 2200 bp. For analogs of lower molecular weight, about 1600 bp are required, whereas for the higher molecular weight analogs, about 2300 bp can be utilized.

In a preferred embodiment, the DNA segment encodes an amino acid sequence corresponding to the sequence in FIGS. 1A, 1B, 1C, 1D, 1E, 1F, and 1G, usually including the leader sequence. More preferably, the segment includes a DNA sequence corresponding to the nucleotide sequence in FIGS. 1A, 1B, 1C, 1D, 1E, 1F, and 1G or a portion thereof, that encodes a protein of this invention. That is, the segment can include the sequence encoding the leader sequence and can also include the untranslated 3'- and 5'-regions, although the non-coding (untranslated) 3'-region is preferably absent.

Although the untranslated 3'-region is preferably absent, the untranslated 5'-region that includes the yeast heat shock promoter is preferably present in some embodiments of the DNA segment. That heat shock promoter is capable of controlling hsp60 expression in both yeast and *E. coli* cells.

The promoter is located in the DNA sequence between the EcoRI recognition site at the 5'-terminus of the yeast chromosomal DNA insert of plasmid p8 whose restriction map is shown in FIG. 5B. As can be seen from the map of FIG. 5B, the promoter is located within the 2.5 kb EcoRI-PstI fragment of the insert and is about 0.8 to 1 kb upstream from the hsp60 start codon (ATG) shown in FIG. 5B. That is the ATG located at nucleotide position +1 of the nucleotide sequence shown in FIGS. 1A, 1B, 1C, 1D, 1E, 1F, and 1G. Thus, the yeast heat shock promoter is located between the 5'-EcoRI recognition site and the start codon for hsp60 and is within the approximately 5 kb EcoRI-EcoRI fragment of yeast chromosomal DNA whose restriction map is shown in FIG. 5B.

In this embodiment, the DNA segment can extend from the 5'-EcoRI site upstream from the hsp60 start codon through nucleotide position 1716 and also through nucleotide position 1783. It is to be understood that the before-described promoter, when present in a DNA sequence segment of an hsp60 analog, is operatively linked to a DNA segment that encodes the hsp60 analog. When so linked, the promoter DNA sequence extends from the 5'-EcoRI recognition site to the start codon of the analog DNA, with the sequences linked in phase, as they also are where hsp60 is itself encoded.

Thus, a DNA segment that consists essentially of the sequence shown in FIGS. 1A, 1B, 1C, 1D, 1E, 1F, and 1G from about position 1 at its 5'-terminus to about nucleotide position 1716 at its 3'-terminus, and is capable of expressing hsp60 constitutes one embodiment of the present invention. A DNA segment consisting essentially of the sequence shown in FIGS. 1A, 1B, 1C, 1D, 1E, 1F, and 1G from a starting nucleotide position at about 67 and ending at about nucleotide position 1716 and capable of expressing hsp60 constitutes another embodiment, of the invention. In another embodiment the segment includes the nucleotides shown in FIGS. 1A, 1B, 1C, 1D, 1E, 1F, and 1G from about nucleotide position −410 to about nucleotide position 1783. It is noted that if neither a plus sign (+) nor a minus sign (−) is utilized before a nucleotide position number, that number is positive.

Nucleotide segments encoding an hsp60 protein can contain a nucleotide sequence that codes for an amino-terminal polypeptide leader sequence such as amino acid residues 1 to about 22 as shown in FIGS. 1A, 1B, 1C, 1D, 1E, 1F, and 1G. Thus, a nucleotide segment forming a structural gene encoding hsp60 consists essentially of the sequence shown in FIGS. 1A, 1B, 1C, 1D, 1E, 1F, and 1G from about position 67 at its 5'-terminus to about position 1716 at its 3'-terminus, and can include positions 1 through 66 at its 5'-terminus, as well as the untranslated regions of the gene shown in FIGS. 1A, 1B, 1C, 1D, 1E, 1F, and 1G.

Analogous DNA and RNA sequences that encode the above hsp60 protein or an analog as defined before are also contemplated. An analogous DNA or RNA sequence that encodes a before-described hsp60 analog need not share the before-stated percentages of identity between hsp60 and an analog due to the redundancies in the genetic code and differences between hsp60 and its analogs.

DNA segments that encode hsp60 and analogous proteins can be synthesized by chemical techniques, for example, the phosphotriester method of Matteucci et al., *J. Am. Chem. Soc.*, 103:3185 (1981). (The disclosures of the art cited herein are incorporated herein by reference.) Of course, by chemically synthesizing the coding sequence, any desired modifications can be made simply by substituting the appropriate bases for those encoding the native amino acid residue sequence. However, DNA molecules including sequences identical to those shown in FIGS. 1A, 1B, 1C, 1D, 1E, 1F, and 1G are preferred.

Furthermore, DNA segments consisting essentially of structural genes encoding an hsp60 protein can be obtained from DNA molecules containing those genes that are present in eucaryotic cells. For example, isolation of the gene encoding hsp60 from Sacchromyces cerevesiae is described in detail herein. Since the sequence is now known, and illustrated in FIGS. 1A, 1B, 1C, 1D, 1E, 1F, and 1G, probes corresponding to a portion of the sequence (or its complementary strand) can be used to isolate the gene from a library or to obtain appropriate genes in other cells as was done herein.

A DNA segment that includes a DNA sequence encoding hsp60 can be prepared by operatively linking (ligating) the sequence to a replication (cloning) vector using well known methods. That vector is thereafter utilized to transfect appropriate cells such as those of *E. coli*, yeast or mammals to replicate the DNA and thereby make more of it.

The replicated DNA can thereafter be collected, operatively linked into an expression vector and that vector transfected into appropriate cells as above to express hsp60. The vector used for replication can also be used for expression in some instances, as is also well known, and discussed in greater detail below.

C. DNA Constructs

The recombinant DNA molecules of the present invention can be produced by operatively linking a vector to a DNA segment of the present invention or to an RNA sequence corresponding thereto using well known techniques. A useful vector thus contains its own polynucleotide sequence operatively linked to a polynucleotide sequence segment that encodes hsp60 or an analog thereof, and that vector is preferably a DNA vector. In view of that latter preference, vectors are usually described herein as DNA constructs or DNA vectors.

As used herein, the term "vector" refers to a DNA molecule capable of autonomous replication in a cell and to which another DNA segment is operatively linked so as to bring about replication of the attached segment. Vectors capable of directing the expression of hsp60 or analog genes are referred to herein as "expression vectors". Thus, a DNA construct is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the hsp60 or analog structural gene included in DNA segments to which it is operatively linked.

In preferred embodiments, a vector contemplated by the present invention includes a procaryotic or eucaryotic replicon; i.e., a DNA sequence having the ability to direct autonomous replication and maintenance of the recombinant DNA molecule extrachromosomally in a procaryotic or eucaryotic host cell, such as a bacterial or yeast host cell, transformed therewith. Such replicons are well known in the art. In addition, those embodiments also include a gene whose expression confers a selectible marker such as drug resistance to a bacterial host transformed therewith. Typical bacterial drug resistance genes are those that confer resistance to ampicillin or tetracycline.

Those vectors that include a replicon such as a procaryotic replicon can also include an appropriate promoter such as procaryotic promoter capable of directing the expression (transcription and translation) of the genes in a bacterial host cell, such as *E. coli*, transformed therewith. Similarly, where a eurcaryotic replicon is used, the vector also contains an eurcaryotic promoter such as the Gal 1 promoter for use in yeast cells. As noted previously, the yeast heat shock promoter located about 0.8 to 1 kb upstream of the hsp60 start codon and within the EcoRI-EcoRI approximately 5 kb yeast chromosomal DNA insert shown in FIG. 5B is particularly preferred.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC8, pUC9, pBR322 and pBR329 available from Biorad Laboratories, (Richmond, Calif.) and pPL and pKK223 available from Pharmacia, Piscataway, N.J. Additional vectors are discussed herein.

Eucaryotic cell expression vectors are also well known in the art and are available from several commercial sources. Typical of such vectors are pSVL and pKSV-10 (Pharmacia), pBPV-1/pML2d (International Biotechnologies, Inc.), and pTDT1 (ATCC, #31255) and YEp352 [Hill et al., *Yeast*, 2:163–167 (1986)]. YEp352 is a shuttle vector that can be used in both procaryotic (*E. coli*) and eucaryotic (yeast) cells.

In preferred embodiments, the eucaryotic cell expression vectors used to construct the recombinant DNA molecules of the present invention include a selectable marker that is effective in an eucaryotic cell. A preferred selectable marker are the URA 3 and HIS 3 genes used herein.

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

D. Transformed Cells and Cultures

The present invention also relates to a host cell transformed with a polynucleotide vector construct of the present invention. The host cell can be either procaryotic or eucaryotic. Bacterial cells are preferred procaryotic host cells and typically are a strain of *E. coli* such as, for example the *E. coli* strains DH5 available from Bethesda Research Laboratories, Inc., Bethesda, MD, and RR1 available from the American Type Culture Collection (ATCC) of Rockville, MD (No ATCC 31343). Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 available from the ATCC as CRL 1658, and the S. cervisae strain RP11 that is deficient in endogenous cytosolic ornithine transcarbamylase (OTC) used herein. This strain is described in Cheng et al., *Proc. Natl. Acad. Sci. USA*, 84:4063–4067 (1987).

Transformation of appropriate cell hosts with a DNA construct of the present invention is accomplished by well known methods that typically depend on the type of vector used. Transformation in yeast cells is discussed specifically herein. With regard to transformation of procaryotic host cells, see, for example, Cohen et al., *Proc. Natl. Acad. Sci. USA*, 69:2110 (1972); and Maniatis et al., Molecular Cloning, A Laboratory Manual, Cold Spring Harbor Laboratory, Cold Spring Harbor, N.Y. (1982). Transformation of yeast cells is described herein and in Sherman et al., Methods In Yeast Genetics, A Laboratory Manual, Cold Spring Harbor, N.Y. (1986). The particular transformations in yeast were typically carried out herein using the lithium method of Ito et al., *J. Bacteriol.*, 153:163–168 (1983). The method of Beggs, *Nature*, 275:104–109 (1978) is also useful. With regard to transformation of vertebrate cells with retroviral vectors containing rDNAs, see, for example, Sorge et al., *Mol. Cell. Boil.*, 4:1730–37 (1984); Graham et al., *Virol.*, 52:456 (1973); and Wigler et al., *Proc. Natl. Acad. Sci. USA*, 76:1373–76 (1979).

Successfully transformed cells; i.e., cells that contain a DNA construct of the present invention, can be identified by well known techniques. For example, cells resulting from the introduction of an expression construct of the present invention can be grown to produce hsp60 or analog. Cells can be harvested, lysed and their DNA content examined for the presence of the DNA using a method such as that described by Southern, *J. Mol. Boil.*, 98:503 (1975) or Berent et al., *Biotech.*, 3:208 (1985). Alternatively, the presence of hsp60 or analog in the supernatant can be detected using anti-hsp60 antibodies as described herein.

In addition to directly assaying for the presence of rDNA, successful transformation can be confirmed by well known immunological methods when the rDNA is capable of directing the expression of hsp60 or an analog. For example, cells successfully transformed with an expression vector produce proteins displaying hsp60 antigenicity. Samples of cells suspected of being transformed are harvested and assayed for hsp60 or an analog using antibodies specific for hsp60.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains biologically active hsp60 or an analog.

Nutrient media useful for culturing transformed host cells are well known in the art and can be obtained from several commercial sources.

E. Methods

The before-discussed DNA and DNA constructs are useful for the preparation of hsp60 or an analog thereof. hsp60 or its analog is utilized in an aqueous composition in vitro for assembling non-functional protein subunits into a functional oligomeric protein complex, as well as for converting inactive forms of monomeric proteins or protein subunits into active forms of those molecules.

Non-functional protein subunits and inactive forms of monomeric proteins and protein subunits include molecules that must be enzymatically processed as by hydrolytic cleavage prior to becoming functional or active, as well as denatured forms of such proteinaceous materials. The denatured protein forms contemplated include those forms that are improperly folded as occurs with urea and similar denaturations, and exclude chemically denatured forms as where a protein molecule is acylated or otherwise reacted or hydrolyzed to a molecular weight at which it cannot be functional or active.

Functionality of assembled, previously non-functional protein subunits can be assessed by usual biological assays for the functional protein. Exemplary of such proteins is ornithine transcarbamylase (OTC), a homotrimer enzyme, whose functionality or lack thereof can be assayed using a substrate for the enzyme such as ornithine.

As is well known in the art, proper three-dimensional folding of protein molecules is usually required for the protein to be active. In addition, many proteins are translated in nature or by recombinant techniques in an inactive, precursor form such as in zymogenic enzymes that are activated post-translationally by the action of one or more enzymes or other molecules. OTC is also exemplary of the type that not only has to be assembled to be active, but also undergoes post-translational cleavage reactions from a precursor form to the mature molecular form that is lower in relative molecular mass than is the precursor prior to assembly. The beta-subunit of ATPase is another protein molecule whose precursor is cleaved prior to assembly of the completed enzyme complex, which contains two sets of five subunits each. The Rieske Fe/S protein is monomeric, but also undergoes post-translational events prior to its becoming functionally active.

Without wishing to be bound by theory, it is believed that the hsp60 molecule and its analogs act as a molecular scaffold or template to which the non-functional or inactive material binds, and on which proper folding and post-translational processing of proteins or protein subunits takes place to form the active forms of such proteins after dissociation from hsp60, or from which properly formed (folded and/or processed) protein subunits can dissociate to form active, functional oligomeric protein complexes. This is especially the case for mitochondrial proteins.

Thus, another aspect of the present invention is a method of assembling non-functional protein subunits of one or more amino acid residue sequences into a functional oligomeric protein complex. In accordance with this method, non-functional protein subunits are admixed in vitro to form an aqueous admixture with a biologically operative, aqueous yeast mitochondrial matrix preparation that contains hsp60 or an analog thereof in an amount of at least about twice the amount of hsp60 than the amount of hsp60 naturally present after heat shock, and more preferably at least about 50 micrograms (ug) at least of per milligram (mg) of total mitochondrial matrix protein, up to about 10 weight percent of hsp60 or analog based upon total mitochondrial matrix protein present. That admixture is maintained under biological culture conditions for a time period sufficient for the subunits to bind to the hsp60 or analog molecule, be processed and folded properly, and to dissociate therefrom to form a functional aligomeric protein complex. That functional complex can thereafter be recovered. Recovery is not essential and the functional protein complex can be used in the solution in which it is made.

It is noted that normal yeast mitochondrial matrix preparations contain hsp60. However, the amount of that protein naturally present in such preparations, even after heat shock, is typically about 10 to about 20 ug/mg. A contemplated matrix preparation contains at least about twice the amount of hsp60 or an analog that is naturally present, even after heat shock.

Biologically operative mitochondrial matrix preparations are themselves well known in the art. Exemplary preparations are described in Cheng et al., *Proc. Natl. Acad. Sci. USA*, 84:4063–4067 (1987); and McMullin et al., *Mol. Cell. Biol.* 8:371–380 (1988). A further illustrative mitochondrial matrix preparation is illustrated hereinafter. It is understood that a contemplated matrix preparation is substantially free of whole cells and nuclear materials such as DNA, and is also typically free of cellular membrane proteins and lipids.

The mitochondrial matrix preparation preferably contains only the proteins of the matrix. However, whole mitochondria can be used, as can a preparation from which the outer membrane is absent. Such preparations are free of the outer membrane and intermembrane fluid, and can be prepared by treatment of mitochondria with osmotic shock or with a phospholipase enzyme, followed by centrifugation as in a density gradient to provide particles of inner membrane and matrix. Treatment of the recovered inner membrane particles with detergent releases the matrix and solubilizes components of the inner membrane. Such preparations are biologically operative in that the matrix proteins are not denatured or otherwise inactivated.

The admixture is maintained under biological culture conditions, e.g., at a temperature of about 1° C. to about 40° C. and in an appropriate buffer at a pH value of about 7.0 to about 7.5. The time of maintenance; i.e., the time sufficient to form a functional oligomeric protein complex, can vary widely, depending upon the protein subunits used and protein complex sought, as well as the temperature. Typical times of maintenance are about 5 minutes to about 25 hours. More usual times are about 30 minutes to about 10 hours.

The functional oligomeric protein complex can be recovered from the reaction admixture by a number of manners well known to skilled workers. The manner selected is often determined by the protein complex itself. Exemplary procedures include affinity chromatography and sucrose density gradient centrifugation. Functionality of a recovered protein complex is assessed with standard techniques.

A method of converting an inactive form of a monomeric protein or protein subunit into an active form of such a molecule is also contemplated. Here, the inactive monomer or subunit is admixed in vitro with a biologically active aqueous mitochondrial matrix preparation containing added hsp60 or analog as described before. That admixture is maintained under biological culture conditions for a time period sufficient for the inactive form to become active; i.e., bind to the hsp60 or analog molecule, be processed, folded properly and dissociate, as discussed before. That active form is thereafter recovered, as discussed previously.

Each of the above methods can be improved by the presence of one or both of the proteins expressed by vectors p1 and 12 discussed hereinafter. Each of those expression products is also a yeast mitochondrial protein and are consequently present in a mitochondrial preparation, as is yeast hsp60. However, as with hsp60 or an analog molecule, the amount of either transcription product present in the reaction admixture is in excess of that normally present in a matrix preparation. Here, the amount of the translation product of vector p1, is also about 40 ug/mg to about 10 percent of the total mitochondrial matrix protein, whereas for the translation product of vector p12, the amount is about 40 ug/mg to about 10 percent of the total mitochondrial matrix protein.

In still further method aspects of the invention, a mitochondrial matrix preparation alone is utilized in the absence of admixed hsp60 or analog, or the translation products of plasmids p1 and p12, to assemble non-functional protein subunits or convert an inactive form of a monomeric protein or protein subunit into a functional oligomeric protein complex or active protein. The steps of such methods are substantially as discussed before except that the admixed proteins are present in their natural concentrations.

In each of the above methods, the matrix preparation with or without added hsp60 or analog (or p1 or p12 translation products) (total matrix protein preparation) is present in an amount effective to functionalize or activate the admixed non-functional protein subunits or monomeric protein molecule or subunit molecules, respectively. That effective amount can vary widely depending, inter alia, upon the temperature utilized, the amount of admixed non-functional or inactive material and the rate at which it is desired for the reaction to proceed.

Typically, the non-functional protein subunits or monomeric protein molecules or protein subunit molecules are present at a weight ratio relative to the total protein of the matrix preparation, including added hsp60 or analog as well as the translation products of vectors p1 and p12, when present, of about 1 to about 20 parts of the former relative to about 200 to about 2000 parts of the latter, total matrix preparation. More preferably, the weight ratio is about 5 to about 10 parts relative to about 300 to about 1000 parts, in the order mentioned.

Total protein concentration in the aqueous composition utilized in an above in vitro method is about 10 to about 70 milliliter (mg/ml). More preferably, that concentration is about 30 to about 50 mg/ml. It is noted that since the total matrix preparation constitutes about 90 or more weight percent of the protein of the admixture, one can base the protein concentration upon the protein of the total yeast mitochondrial matrix preparation.

EXAMPLES

The following examples are intended to illustrate, but not limit, the present invention.

Example 1
Isolation of a Mutant Defective in Assembly/Folding

A strategy for isolation of conditional yeast mutants affecting the mitochondrial-import machinery illustrated in FIG. 2. The strategy was based on the presumption that obstruction of import of essential metabolic enzymes that reside within mitochondria would be lethal. It was based also on the observation that when the subunit precursor of the human mitochondrial matrix enzyme ornithine transcarbamylase (OTC) was expressed in yeast, the precursor followed the same pathway of import employed by endogenous yeast mitochondrial precursors.

Temperature-sensitive (ts) lethal mutants were derived from a Saccharomyces cerevisiae yeast strain that is defective at the yeast OTC locus (arg 3) but that contains in its URA 3 locus an integrated segment containing the human OTC coding sequence joined with an inducible yeast Gal 1 promoter (GALOTC strain). To identify temperature shock (ts) mutants affected in mitochondrial import, expression of human OTC at non-permissive temperature was induced, and whether OTC enzyme activity could be produced under those conditions was examined. A group of mutants that failed to demonstrate activity was collected.

Those mutants were further analyzed by immunoblot analysis of extracts with anti-OTC antiserum. Two classes of mutant were distinguished. In one class, precursors of both human OTC and endogenous yeast mitochondrial proteins accumulated at non-permissive temperature. Complementation analysis of this class revealed three groups, called mif 1, 2, and 3 (mitochondrial import function mutants). mif 1 and 2 were shown to encode the two subunits of the mitochondrial processing protease, the processing enhancing protein (PEP) and the matrix processing peptidase (MPP), respectively.

In a second class of ts lethal mutants, the mature-size OTC subunit was observed at non-permissive temperature ($M^+$) but no OTC enzyme activity could be detected ($A^-$). Three different molecular defects could explain such a phenotype: 1) A defect in translocation, leaving OTC subunits only partway translocated through the mitochondrial membranes, in a position where they were able to be cleaved by the matrix processing enzyme to a mature size but were not able to be further translocated through the membranes to a position where they could contact each other to assemble into the active homotrimeric enzyme; 2) A defect in the OTC subunit itself, allowing OTC subunits to be completely translocated to the matrix space but blocking their assembly into enzymatically active homotrimer; 3) A defect in a mitochondrial component that normally plays a role in assembly of subunits reaching the matrix space. The second type of defect would not lead by itself to a lethal phenotype because OTC activity is not required for growth of cells as long as arginine is provided in the growth medium. However the first and third types of defect could produce a lethal phenotype because these defects could involve components likely to play a general role in import.

To determine whether any of the mutants exhibited a defect of either translocation or assembly, each mutant was cured of the human OTC sequence, transformed with a new Gal-OTC segment, and tested at 37° C. for both the size of OTC subunits and the presence of enzyme activity. More specifically, each mutant was first mated with an arg 3 strain and sporulated. Tetrads were then examined for 2:2 ts lethal behavior to demonstrate that a single lethal mutation was present in the original mutant strain. Spores were also tested for absence of the URA 3 gene in order to identify ts spores in which the ts mutation had segregated away from the original integrated Gal-OTC-URA 3 segment.

Ts ura$^-$ spores were transformed with a new Gal-OTC-DRA 3 segment. The ura$^+$ transformants were examined for OTC activity after galactose induction at 37° C. Nine out of ten mutants exhibited normal levels of activity, suggesting that they had originally harbored two mutations, one a ts lethal mutation that does not directly affect the import pathway, and a second mutation affecting the human OTC sequence.

One of the ten mutants, however, alpha-143, also referred to as ts143, behaved differently. As in the other mutants, mature size OTC subunits were detected following induction at 37° C. However, in this mutant no OTC activity was detected. When examined at the permissive temperature, 23° C., this mutant behaved like wild-type. Both mature subunit and OTC activity were detected. ts143 thus contains a single ts lethal mutation that affects the ability of mature-size wild-type human OTC subunits to produce enzyme activity.

To determine whether OTC subunits in the ts143 cells had assembled into homotrimeric enzyme, an assay was carried out using the OTC substrate analogue, delta-N phosphonoacetyl L-ornithine (PALO). Total cell extracts were prepared from both ts143 and wild-type cells grown for 2 hours at 37° C. in galactose medium. The extracts were applied to columns containing PALO linked to epoxy-Sepharose. Column eluents were collected and immunoprecipitated with anti-OTC antiserum. The precipitates were solubilized, fractionated in SDS-PAGE, and the gel immunoblotted with anti-OTC antiserum.

when wild-type extracts were applied to the column, no mature size subunit was observed in the flow-through fraction (CE and BK), consistent with the ability of the substrate analogue to quantitatively bind assembled OTC enzyme. In contrast, when an extract of ts143 cells was applied, the flow-through was found to contain both precursor and mature size OTC subunits, in an amount corresponding to that applied.

Both wild-type and ts143 columns were next washed with buffer containing 40 mM KCl (SW). No OTC submits eluted from either column, indicating absence of nonspecific binding.

The columns were finally washed with the OTC substrate carbamyl phosphate (Cp). An amount of mature-size OTC subunit corresponding approximately to that originally applied eluted from the wild-type column. In the case of the ts143 column, neither OTC precursor nor mature OTC subunit was detected, demonstrating the quantitative passage of subunits through the column during the initial application of extract. Therefore, mature-size wild-type human OTC subunits are produced in ts143 cells at 37° C., but fail to assemble into homotrimeric, catalytically active, OTC enzyme.

Example 2

Assembly of an Endogenous Yeast Mitochondrial Protein was Affected in ts143 Cells at Non-permissive Temperature.

An assay for assembly of the nuclear-coded matrix protein F1ATPase beta-subunit into ATPase complex was carried out. This assay utilized the previous observation that following chloroform ($CHCl_3$) extraction of a mitochondrial suspension, assembled F1ATPase complex partitions into the aqueous phase whereas non-assembled subunits of the ATPase partition into the organic layer. ts143 and wild-type cells were grown at 23° C., then shifted to 37° C. and pulse-labeled with $^{35}S$-methionine. After 2 hours, the cells were harvested and mitochondria prepared.

One-half of each of the preparations was directly solubilized, then immunoprecipitated with anti-F1beta (F1B) antiserum. The remaining half of each preparation was extracted with an equal volume of chloroform and the aqueous phase immunoprecipitated. The precipitates were analyzed in SDS-PAGE by autoradiography as shown in FIG. 3B. This chloroform extraction procedure is substantially that reported in Douglas et al., *J. Biol. Chem.*, 252:8333–8335 (1977), as applied to the present system.

Following extraction of wild-type (wt) mitochondria with chloroform, mature F1B subunit was recovered nearly quantitatively in the aqueous phase, reflecting assembly of mature subunits into the ATPase complex. In striking contrast, following chloroform extraction of ts143 mitochondria, virtually no mature F1B subunit was detectable in the aqueous phase. Thus, mature F1B subunit produced in the ts143 mutant at non-permissive temperature had failed to assemble into the F1ATPase complex.

Example 3
Monomeric Mitochondrial Proteins Failed To Assume An Active Conformation in ts143 Cells Following observation that two different nuclear-encoded mitochondrial proteins in the ts143 mutant reached mature size but failed to assemble into corresponding oligomeric enzymes, whether mitochondrial proteins that assume a monomeric form in the mitochondrial matrix would also be affected was studied. Two such proteins were examined.

First, the Rieske Fe/S protein was studied. This nuclear-coded polypeptide is normally translated in the cytosol as a precursor and imported to the matrix space. Following cleavage of an amino-terminal portion of its signal peptide by the matrix processing protease, the Fe/S protein binds an atom of iron, is cleaved by a second matrix-localized protease, and exits through the inner mitochondrial membrane to reach its final destination in the intermembrane space.

The fate of the Fe/S protein in both wild-type and ts143 cells was examined by immunoprecipitation of extracts of cells radiolabeled at 37° C. When wild-type cells were examined, virtually all of the immunoprecipitable Fe/S protein was observed in the mature size. In contrast, in ts143 cells, only the intermediate-size species was detected. This abnormality could result from: 1) defective translocation of Fe/S protein molecules through the mitochondrial membranes; the molecules might reach only an intermediate position, where the signal portion has reached the matrix space and been cleaved by the matrix processing protease, but the remainder of the protein remains behind, in a membrane-spanning topology, unable to proceed to the subsequent steps of biogenesis; 2) defective complexing of matrix-localized molecules with iron; if complexing with iron normally directs the intermediate-sized protein into a conformation required for recognition by the second processing enzyme, then a defect of complexing, which may itself require conformational alteration, would block the second step of proteolytic cleavage; 3) defective proteolytic processing of complexed molecules; this could result from failure of the complexed protein to assume a conformation that can be recognized by the processing enzyme or from a defect in the processing enzyme itself.

To define the involved step, a second protein, cytochrome $b_2$, that pursues a pathway of biogenesis divergent from that of the Fe/S Rieske protein, was analyzed. Like the Rieske protein, cytochrome $b_2$ is translated in the cytosol as a precursor, imported to the matrix space, and the amino-terminal portion of its signal peptide is cleaved by the matrix processing protease. However, this polypeptide is then directly targeted back through the inner membrane to the intermembrane space. There, the remainder of the leader peptide is cleaved by a processing protease distinct from those located in the matrix space. The protein then anchors in the inner membrane via a carboxy-terminal hydrophobic domain. when ts143 cells were radiolabeled at 37° C. and cell extracts immunoprecipitated with anti-$b_2$ antiserum, only the intermediate-sized form was observed (i), with none of the mature-sized (m) protein or the precursor (pre) seen as is the case with the wild-type (wt) cells.

The abnormality in this case could result from: defective translocation of molecules to the matrix; or failure of fully-translocated intermediate-size $b_2$ molecules to be redirected through the inner membrane. The second phenotype could result either from a failure of conformational alteration, presumed to be necessary for translocation back through the inner membrane, or from a defect in the translocation apparatus itself.

The latter defect could not by itself also explain the results with the Fe/S protein because that protein never reaches the step of inner membrane translocation. That is, obstruction of Fe/S biogenesis occurs before a second processing step, which precedes inner membrane translocation. Thus, for the defect in ts143 to similarly affect both Fe/S protein and cytochrome $b_2$, the affected step involves either translocation into the matrix space or conformational alteration mediated within the matrix compartment.

To distinguish the defect in ts143, the same yeast mitochondrial subunits that had been examined in intact cells were synthesized in vitro, as precursors, and incubated with mitochondria isolated from cultures of ts143 grown either at permissive or nonpermissive temperature. The methods used for these studies were substantially those reported in Hartl et al., *Cell*, 51:1027–1037 (1987) and Hartl et al., *Cell*, 47:939–951 (1986) in which in vitro import studies into Neurospora crassa mitochondria of cytochrome b2 and Rieske Fe/s protein, respectively, were reported.

When F1-beta precursor was incubated with wild-type (wt) mitochondria prepared from cells grown at 37° C., the subunit was converted to its mature size. When proteinase K was added to the mixture after incubation, it failed to digest the mature subunit, indicating localization inside the organelles. When the same incubations were carried out using mitochondria prepared from a 37° C. culture of ts143, the mature subunit and a small amount of precursor were observed to be protected from digestion by the added protease. This excludes a defect of translocation, which would have left the mature subunit susceptible to proteolysis.

To determine the state of assembly of the imported mature F1-beta subunits, the organelles were extracted with chloroform. Both the supernatant and organic phases were solubilized and immunoblotted with anti-F1-beta antiserum. When a wild-type sample was extracted, greater than 50 percent of the total mature F1-beta subunits partitioned into the aqueous phase, indicating assembly of the imported subunit into the ATPase complex. When the ts143 sample was extracted, virtually no mature-sized subunit was detected in the aqueous phase with substantially all of the subunits being in the chloroform phase, indicating that the imported subunit had failed to assemble.

Next, the behavior of precursors of Fe/S protein and cytochrome $b_2$ was examined. Here, when Fe/S protein was incubated with mitochondria from the mutant (ts143), it reached only intermediate size, corresponding to the results with intact cells.

In the case of cytochrome $b_2$, the effects were less marked than with intact cells. The repeatable observation was that a smaller amount of mature subunit was produced by mutant mitochondria compared to the wild-type.

For both proteins, intermediate-sized species observed with the mutant mitochondria were protected from digestion by added trypsin, indicating that the subunits of these two proteins, like F1-beta, had been completely translocated to the matrix compartment. Therefore, the defect in ts143 affected a mechanism by which proteins assume appropriate conformations following their entry into the matrix space. Those conformations are required for component subunits to assemble into their respective oligomeric proteins and to assume biological activity.

Example 4
Characterization of the Mutation in the hsp60 Gene

To further characterize the mutation in ts143, the strain was subjected to genetic crosses. First, it was mated at 23° C. with a wild-type strain of the opposite mating type and the diploids shifted to 37° C. Normal growth was observed at the high temperature, and the amount of OTC enzyme activity detected following galactose induction was similar to that detected in the original GALOTC parent strain. This lack of mutational effect in a heterozygous diploid indicates that the mutation in ts143 is recessive.

The ts143 strain was next crossed with each of three other recessive lethal mutants affecting the mitochondrial import pathway, mif 1, 2, and 3. The first two of these mutants affect the subunits of the matrix protease, while the third affects a putative cytosolic factor. Diploid cells from all three crosses grew normally at 37° C., indicating that ts143 belongs to a distinct complementation group, designated mif 4 (ts143). The observation of distinct genetic behavior of ts143 agrees with the distinct phenotype of this mutant.

To isolate a wild-type copy of the gene affected in ts143, the haploid strain was transformed with a CEN library substantially identical to that of ATCC Deposit No. 37415 prepared using shuttle vector YCp50 (ATCC 37419) [Rose et al., Gene, 60:237–243 (1987)], containing fragments of yeast genomic DNA inserted into a plasmid that contains both a centromere sequence and a URA3 marker. The particular library utilized was a retained library that was obtained directly from Dr. Peter Novick, a co-author of the above Rose et al. article. That library was therefore substantially the same as ATCC No. 37415.

In one strategy of genetic rescue, URA$^+$ transformants were selected at 23° C., then replica plated to rich medium (YPD) at 37° C. In a second strategy, yeast cells were directly plated on YPD medium at 37° C. following transformation.

In both cases, DNA was prepared from colony-purified transformants and used to transform E. coli to ampicillin-resistance. Plasmid DNAs were then isolated and characterized by restriction analysis. Plasmids from the strategy involving initial URA selection at 23° C. followed by replica plating to 37° C. all shared several restriction fragments containing inserted yeast genomic DNA. Plasmids from the strategy involving direct plating at 37° C. exhibited not only this pattern in several isolates but also other distinct restriction patterns each isolated independently more than once.

Next, whether any of these rescuing plasmids might encode a heat shock protein was studied. Yeast DNA inserts from the plasmids were nick-translated and used to probe blots containing RNA prepared from wild-type yeast grown at 23° C. and either maintained at this temperature or exposed first to an incubation at 42° C. for one hour. The results of that study with the insert from a plasmid designated p8 belonging to the unique group of plasmids obtained by both rescue strategies indicated an increase in the amount of assayed-for RNA in the cells incubated at the higher temperature than those incubated at the lower temperature. Plasmid P8 thus contains plasmid YCp50plus the gene for the rescuing protein.

The p8 insert identifies a poly A+ mRNA of approximately 1800 nucleotides. The amount of this species present in a preparation of total RNA, was increased 2- to 3-fold by 42° C. incubation. Both the size and heat inducibility of this message indicated that it might encode an approximately 64 kilodalton (K) heat shock protein recently identified in mitochondria of yeast by McMullin et al., Mol. Cell Biol, 8(1):371–380 (1988).

To determine whether this was the case, the restriction map of p8, shown schematically in FIG. 5B, was compared with the map of lambda-hsp60, a yeast plasmid isolated as described hereinafter from a lambda-gt11 library using an antiserum directed against a homologous 58K mitochondrial heat shock protein of T. thermophila [anti-hsp60(T.t.). The maps of the two cloned yeast segments precisely overlapped.

To confirm identity of the two sequences, a region of p8, extending from a Pst I site (see arrow in FIG. 5B), was subjected to DNA sequence analysis. The p8 sequence was compared with that from the corresponding region in lambda-hsp 60, which lies within the protein coding region. The two sequences were identical.

To establish that HSP60 is the gene affected by mutation in ts143 cells, and thus to exclude that transfer of an additional copy of HSP60 could rescue a mutation occurring at a different locus, a homologous recombination study was carried out. The p8 plasmid was resected with restriction enzymes SmaI and BglII to remove the centromere sequence. The recircularized derivative plasmid was linearized at a unique BamHI site within the HSP60 coding sequence and transformed into ts143. URA$^+$ transformants were selected and a number were analyzed by DNA blot hybridization using a segment of the HSP60 coding sequence as a probe, to confirm insertion of the cloned HSP60 sequence into the chromosomal homologue.

Two transformants containing such homologous insertions were mated independently with a ura$^-$ wild-type strain, the diploids were sporulated at 23° C. and segregants were examined for ability to grow at 37° C. If the site of the ts143 mutation were in HSP60, then homologous recombination should permit all spores to grow at 37°. If the mutation localized elsewhere in the yeast genome, then homologous recombination into HSP60 should not rescue the mutant phenotype. Rather, the mutant phenotype should simply segregate 2:2. Rigorously, a significant fraction of the spores that contain the homologous insertion and are thus ura$^+$, should nevertheless exhibit the mutant phenotype.

Seventeen tetrads from one diploid and eight from another were examined. The results were unequivocal. All of the spores grew normally at 37° C., including the 50 percent that were ura$^+$. Thus, the mutation in the ts143 strain, responsible for the observed defect of assembly/folding, involves hsp60.

Two additional plasmids obtained from the before-described work were also capable of rescuing ts143 cells. Those two plasmids are designated p1 and p12, and contain about 14 and 13 kilobases, respectively (FIGS. 5C and 5D, respectively). Each of those plasmids contains a gene that is different from the hsp60 gene and also different from the gene for the hsp70 protein discussed in McMullin et al., *Mol. Cell. Biol.* 8:371–380 (1988).

Example 5
Mutation Affects The Hsp60-Containing Complex

In the above examples, the HSP60 gene was shown to be essential for the growth of yeast. The gene encodes an approximately 66K precursor protein that is targeted to the mitochondrial matrix by an amino-terminal cleavable signal peptide. The mature approximately 64K protein bears a striking resemblance to the 65K product of the GroEL gene of *E. coli*, a product required for bacteriophage head assembly and essential for cell viability. This structural and possible endosymbiotic evolutionary relationship of hsp60 to a bacterial protein that appears to participate in molecular assembly adds support to the conclusions from biochemical analysis of ts143, that hsp60 participates in assembly/folding of proteins in the mitochondrial matrix. Like GroEL, hsp64 has been shown to reside in a macromolecular complex: following extraction in its native state it sediments in sucrose gradients to a size position corresponding to greater than monomer, at about 20–25 S in sucrose density gradients; and in electron microscopic analysis of matrix fractions containing the protein, two 7-fold symmetric "doughnuts" are observed, placed one on top of the other.

If the macromolecular complex containing hsp60 is the active mediator of assembly, then alteration of the hsp60 component by mutation might affect the integrity of the complex. To address this possibility, total extracts were prepared from ts143 cultures that had been grown at 23° C. and either maintained at that temperature or shifted to 37° C. for one-half hour. After a low speed centrifugation, extracts were precleared with a 15,000×g spin and the supernatants fractionated in 15–30 percent sucrose gradients.

Both the stained gel and immunoblot analysis indicated that hsp60 in 23° C. extracts migrated to the midportion of the gradient. This result corresponds to that observed with extracts of wild-type yeast. When the 37° C. extract was examined, a much smaller portion of the total hsp60 protein was observed at the mid-position of the gradient. Instead, most of the product was observed in the pellet from the 15,000×g preclearing step.

An identical analysis was also carried out at a time 2 hours after shift of the ts143 culture from 25° C. to 37° C. As shown in FIGS. 6A and 6B, at this time after temperature shift, all of the hsp60 product in the ts143 strain was detected in the pellet fraction (25 and 37). In a control shift study with wild-type yeast, no such result was observed. All of the hsp60 migrated to the midposition of the gradient [McMullin et al., *Mol. Cell. Boil.*, 8:371–380 (1988)].

The behavior of hsp60 leading at 37° C. to its sedimentation into a 15,000×g pellet is not understood. The complex containing the protein may become insoluble and thus precipitated. Alternatively, the complex might somehow have become associated with membranes. It is noted that when both OTC and F1-beta subunits were examined in ts143 cells at 37° C. they also sedimented into the 15,000×g pellet, suggesting that they also might have become insoluble. Whatever the precise alteration, the physical properties of the protein complex containing hsp60 are affected by the hsp60 mutation present in the ts143 strain.

Example 6
Isolation of the Hsp60 Gene

Polyclonal antiserum raised against purified Tetrahymena thermophila hsp60 [anti-HSP60(T.t.); McMullin et al., *Mol. Cell. Biol.* 7:4414–4423 (1987)] was used to isolate a segment of the yeast HSP60 gene, by screening a library of genomic DNA fragments ligated into the phage lambda vector lambda-gt11 (such as ATCC 37194) [Young et al. *Proc. Natl. Acad. Sci. USA* 80:1194–1198 (1983)] for expression of hsp60 -related protein sequences. Nucleotide sequence analysis of a 3.0 kilobase (kb) yeast DNA fragment present in one anti-hsp60(T.t.)-reactive clone revealed an open reading frame coding for a protein homologous to both groEL and Rubisco binding protein (RBP). This DNA fragment was used as a hybridization probe to isolate an overlapping segment of the yeast genome which contained the entire HSP60 coding sequence (FIGS. 1A, 1B, 1C, 1D, 1E, 1F, and 1G).

The sequence of a 1.8 kb region containing HSP60 is presented in FIGS. 1A, 1B, 1C, 1D, 1E, 1F, and 1G along with the derived amino acid sequence. The open reading frame codes for a polypeptide of 572 ($M_r$ 60,830 daltons) amino acids with very strong homology to the conserved family of groEL-related proteins (FIGS. 9A, 9B, 9C, 9D, and 9E,). This open reading frame was defined as the yeast HSP60 gene.

Northern hybridization analyses showed that HSP60 is transcribed into an mRNA of approximately 1.9 kb, a size commensurate with the observed 60K$M_r$ of hsp60 (FIG. 7B). This mRNA is induced two- to three-fold above basal levels when cells are heat stressed at 39° C. for 2 hours, in agreement with the heat shock inducibility of hsp60 [McMullin et al., *Mol. Cell. Boil.*, 7:4414–4423 (1987) and McMullin et al., *Mol. Cell. Boil.*, 8:371–380 (1988)]. Increasing the copy number of HSP60 by transformation with the multicopy plasmid YEphsp60 (FIG. 8B) results in higher concentration of anti-hsp60(T.t)-reactive material in mitochondria, providing further evidence for the identity of this gene.

Comparison of the HSP60 and groEL products (FIGS. 9A, 9B, 9C, 9D, and 9E,) reveals 53 percent amino acid residue identity over the length of the bacterial protein, given five small insertion/deletions in the alignment. Comparison of hsp60 to wheat chloroplast RBP reveals 42 percent identity over the length of the wheat protein, including four insertion/deletions. Approximately one third of the residues are conserved in all three proteins, and there are numerous conservative substitutions. Regions of homology are distributed evenly throughout the lengths of the proteins. One exception occurs at the carboxyl terminus, where the repeated Gly-Gly-Met motif is conserved in both hsp60 and groEL, but not in RBP.

The HSP60 gene product contains an amino terminal extension of approximately 22 amino acids that is not represented in two other members of this gene family. This sequence is characteristic of most known mitochondrial targeting peptides [Hurt et al. *Trends Biochem. Sci.*, 11:204–207 (1986)] in that it contains five basic and no acidic residues, and contains a total of six serine or threonine residues. The presence of this targeting sequence is consistent with the mitochondrial location of hsp60 [McMullin et al., *Mol. Cell. Boil.*, 7:4414–4423 (1987) and McMullin et al., *Mol. Cell. Biol.*, 8:371–380 (1988)].

One-step gene disruption [Rothstein, R. J. *Meth. Enzym.*, 101:202–210 (1983)] was used to construct an allele of HSP60 that is inactive due to insertion of the HIS3 gene (FIG. 8C). The diploid strain a/alpha-W303-Vhsp60 was constructed with one wild-type HSP60 allele and one null allele designated HSP60::HIS3. This strain is homozygous his3⁻, so that the wild-type and null alleles of HSP60 can be scored by histidine auxotrophy and prototrophy, respectively. a/alpha-W303-V-Hsp60 was induced to sporulate. Tetrad products were separated by micromanipulation. In all cases, only two of the four meiotic products from a single tetrad formed colonies, on non-selective media. Replica plating revealed that all surviving progeny required histidine and thus had received the HSP60 allele. Since no haploid cells containing HSP60::HIS3 form colonies. HSP60 is essential for cell viability in yeast. Since the cells were grown at 30° C., the requirement for HSP60 is not limited to heat stress conditions.

The phenotype of ts143 that prevents assembly within mitochondria without affecting either transport into the organelle or cleavage of targeting peptides might be predicted for a mutation in HSP60. Whether ts143 and HSP60::HIS3 were allelic was therefore studied. Preliminary evidence that the two mutations are allelic is that transformation of a ts143 strain with YEpHsp60 restores the ability to grow at non-permissive temperature.

To rule out suppression of ts143 by increased copy number of HSP60, complementation of the two mutations was assayed directly in diploids. The ura3⁻/ura3⁻ diploid a/alpha-W303-VHSP60 was transformed with YEpHSP60. In subsequent manipulations, the presence of extrachromosomal HSP60 is marked by the ura3 gene of the plasmid. Tetrad dissection yielded haploids containing either functional HSP60 or the null allele HSP60::HIS, along with extrachromosomal YEpHsp60. Each haploid was mated to a strain containing ts143 and diploids were selected by complementation of auxotrophies. As expected, the HSP60/ts143 diploid frequently lost YEpHsp60 during mitotic growth, and these uracil-requiring segregants were viable at non-permissive temperature.

In contrast, 100 percent of the mitotic segregants from a HSP60::HIS3/ts143 diploid grown at non-permissive temperature were uracil prototrophs and thus contained extrachromosomal copies of HSP60. Therefore, HSP60::HIS3 and ts143 do not complement one another. Consequently, these two mutations are located in the same genetic element. As described in the previous examples, a different genetic approach also showed that ts143 is an allele of HSP60.

Example 7

Assembly of Non-functional, Denatured Ornithine Transcarbamylase Urea-denatured ornithine transcarbamylase (OTC) that was non-functional as an enzyme was transformed into functional OTC as follows.

OTC was purified by passage through an affinity column prepared from epoxy-Sepharose reacted with delta-N-phosphonacetyl-L-ornithine (PALO), as discussed in Example 1. The purified OTC (25 ug) was denatured by dispersing it in aqueous buffer containing 0.5 ml of 8M urea, 20 mM Hepes and 10 mM dithiothreitol (DTT); the resulting admixture was placed on ice for a time period of 30 minutes.

The mitochondrial matrix preparation utilized was prepared as follows. Wild-type yeast cells were cultured in 3 liters of YPEG medium to mid-log phase, $O.D._{600}$ about 1.0. Cells were harvested on a G-53 rotor, washed once with water, and then treated for 10 minutes with an aqueous buffer solution containing 0.1 M Tris-$SO_4$ pH 8.9, and 10 mM DTT to provide a concentration of about 0.5 grams of cells per ml (g cells/ml) of buffer.

Cells were then washed with a buffer solution containing 1.2 M sorbitol and 20 mM Kpi pH 7.4, and spheroplasted in 0.15 g cells/ml Zymolyase solution (1.2 M sorbitol, 20 mM Kpi pH 7.4, and 1 mg Zymolyase/g of cells) at 30° C. for 45 minutes. Spheroplasts were harvested by centrifugation on an SS-34 rotor at 3000 r.p.m. for 5 minutes at 4° C. The centrifuged cells were washed once with a buffer containing 1.2 M sorbitol, and 20 mM Kpi pH 7.4, resuspended in a buffer containing 0.6 M sorbitol, 20 mM Hepes pH 7.4, and 1 mM PMSF at 0.15 g of cells/ml, and thereafter subjected to Dounce homogenization for 30 cycles.

The resulting cell homogenate was spun in an SS-34 rotor at 3000 r.p.m. for 5 minutes to remove nuclei and cell debris. The cloudy supernatant was then pelleted on the SS-34 rotor at 9000 r.p.m. for 10 minutes. The resulting pellet, which was a mitochondrial fraction of the original cells, was resuspended in a minimal amount of a buffer containing 20 mM Hepes pH 7.4, 1 mM PMSF and 1 mM DTT, and further homogenized with glass beads. The resulting homogenate was transferred into Eppindorf tubes and centrifuged in a minifuge for 10 minutes. The resulting supernatant provided the yeast mitochondrial matrix preparation used below.

The denatured OTC (5 ug) in 200 ul of 8 M urea solution was diluted about one-hundred times using an aqueous buffer containing 20 mM Hepes pH 7.4, 1 mM DTT and 1 mM PMSF, and that also contained either (a) about 400 ug of bovine serum albumin (BSA; control) or (b) about 400 ug of total mitochondrial matrix preparation protein from the above preparation. Each of the above (a) and (b) solutions was separately concentrated in a CENTRICON 30 centrifugal concentrator to a volume of about 100 ul and thereafter returned to its original volume. This procedure, through the assay described below that was carried out immediately after returning the solution to its original volume took about 3–4 hours.

In another study, the before-described OTC-urea solution was diluted to about four volumes with the above buffer containing about 400 ug of (c) BSA or (d) mitochondrial matrix preparation. Each of those solutions was dialyzed against one liter of the buffer solution for a time period of about 18 hours with one change of dialysis buffer. The dialysis and CENTRICON 30 procedures remove the urea.

Each of the resulting solutions (a), (b), (c) and (d) was separately assayed for functional OTC activity using the assay method of Kalousek et al., *J. Biol. Chem.*, 259:5392–5395 (1984). Solutions (b) and (d) that contained the mitochondrial matrix preparation exhibited OTC activity, whereas solutions (a) and (b) that contained BSA exhibited no activity. The activity exhibited by solutions (b) and (d) was relatively minimal, with the dialysis method providing greater functional activity.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A DNA segment consisting, essentially of an isolated, non-chromosomal DNA segment encoding heat shock protein 60 (Hsp60), a protein having a molecular weight between 55,000 and 65,000 by SDS-polyacrylamide gel electrophoresis under denaturing conditions, wherein the Hsp60

(a) has at least 80% identity at the amino acid level with the sequence shown in FIG. 1, and (b) interacts with newly synthesized proteins to fold them into their biologically active conformation.

2. The DNA segment of claim 1 that contains the sequence shown in FIG. 1.

3. The DNA segment of claim 1 that encodes the amino acid residue sequence encoded by nucleotide position 67 through nucleotide position 1716 shown in FIG. 1.

4. The DNA segment of claim 2 that contains a promoter permitting transcription of the sequence encoding Hsp60.

5. The DNA segment of claim 4 wherein the promoter is the heat shock promoter DNA sequence of yeast chromosomal DNA EcoRI-EcoRI fragment of approximately 5 kb whose EcoRI and PstI restriction map is shown in FIG. 5B, said promoter sequence extending from said 5'-EcoRI site to the start codon of said Hsp60 DNA sequence segment.

6. A vector which autonomously replicates in a cell, said vector containing a polynucleotide sequence segment that encodes Hsp60, wherein the Hsp60

(a) has at least 80% identity at the amino acid level with the sequence shown in FIG. 1, and (b) interacts with newly synthesized proteins to fold them into their biologically active conformation.

7. The vector of claim 6 wherein said vector is a DNA vector that directs expression of said Hsp60.

8. The vector of claim 7 that contains about 1600 to about 2300 DNA base pairs that encode Hsp60.

9. The vector of claim 8 that is a shuttle vector and can replicate in both eucaryotic and procaryotic cells.

10. The vector of claim 8 wherein said DNA encodes the amino acid residue sequence shown in FIG. 1 from amino acid residue 22 through amino acid residue 572.

11. A transformed host cell containing a vector that autonomously replicates therein, said vector containing a polynucleotide sequence segment that encodes Hsp60, wherein the Hsp60

(a) has at least 80% identity at the amino acid with the sequence shown in FIG. 1, and (b) interacts with newly synthesized proteins to fold them into their biologically active conformation.

12. The transformed host cell of claim 11 wherein said vector is a DNA vector that directs expression of said Hsp60 in said host cell.

13. The transformed host cell of claim 12 wherein said vector encodes the amino acid residue sequence shown in FIG. 1 from amino acid residue 22 through amino acid residue 572.

* * * * *